US012611500B1

(12) United States Patent
Huszar et al.

(10) Patent No.: US 12,611,500 B1
(45) Date of Patent: Apr. 28, 2026

(54) SYSTEMS, DEVICES, AND METHODS INCLUDING FILTERS FOR USE WITH THROMBECTOMY PROCEDURES

(71) Applicant: Endovascular Engineering, Inc., Menlo Park, CA (US)

(72) Inventors: Hillary Kaye Huszar, Redwood City, CA (US); David Snow, San Carlos, CA (US); Scott J. Baron, Menlo Park, CA (US); Michael Rosenthal, Menlo Park, CA (US)

(73) Assignee: Endovascular Engineering, Inc., Menlo Park, CA (US)

( * ) Notice: Subject to any disclaimer, the term of this patent is extended or adjusted under 35 U.S.C. 154(b) by 0 days.

(21) Appl. No.: 19/230,774

(22) Filed: Jun. 6, 2025

Related U.S. Application Data

(62) Division of application No. 19/066,822, filed on Feb. 28, 2025, now Pat. No. 12,440,615.

(Continued)

(51) Int. Cl.
A61M 25/00 (2006.01)
A61M 1/00 (2006.01)
(Continued)

(52) U.S. Cl.
CPC .......... A61M 1/79 (2021.05); A61M 25/0097 (2013.01); A61M 39/24 (2013.01);
(Continued)

(58) Field of Classification Search
CPC .... A61M 1/79; A61M 25/0097; A61M 39/24; A61M 2039/2473; A61M 2205/3334; A61M 2205/3337; A61B 2017/22079
See application file for complete search history.

(56) References Cited

U.S. PATENT DOCUMENTS 4,033,345 A * 7/1977 Sorenson ............ A61M 1/3627
604/28
4,083,786 A 4/1978 Tsuda et al.
(Continued)

FOREIGN PATENT DOCUMENTS

CN 105288766 A 2/2016
CN 105288821 A 2/2016
(Continued)

OTHER PUBLICATIONS

[Author Unknown] "Penumbra—Indigo System." [product catalog] Penumbra, Inc. Oct. 2016; 10013(Rev C); 5 pages.
(Continued)

*Primary Examiner* — Susan S Su
*Assistant Examiner* — Erin A Kim
(74) *Attorney, Agent, or Firm* — COOLEY LLP

(57) ABSTRACT

Described herein are systems, devices, and methods for methods for filtering fluids received from a patient. In embodiments, an apparatus can include a fluid conduit configured to receive a volume of fluid from a patient, the volume of fluid including a plurality of particulates having different sizes; a container including an inlet near a first end and an outlet near a second end opposite the first end, the inlet being fluidically coupled to the fluid conduit, the container defining a reservoir configured to receive the volume of fluid from the fluid conduit via the inlet; first and second filters; and an outlet being couplable to a vacuum source that can generate negative pressure to draw at least a portion of the volume of fluid within the reservoir through the second filter and into the vacuum source.

20 Claims, 13 Drawing Sheets

Related U.S. Application Data

(60) Provisional application No. 63/712,962, filed on Oct. 28, 2024.

(51) Int. Cl.
   *A61M 39/24*    (2006.01)
   *A61B 17/22*    (2006.01)

(52) U.S. Cl.
   CPC .............. *A61B 2017/22079* (2013.01); *A61M 2039/2473* (2013.01); *A61M 2205/3334* (2013.01); *A61M 2205/3337* (2013.01); *A61M 2205/583* (2013.01)

(56)                 References Cited

U.S. PATENT DOCUMENTS

| | | | |
|---|---|---|---|
| 5,215,519 | A | 6/1993 | Shettigar |
| 5,279,550 | A | 1/1994 | Habib et al. |
| 5,607,411 | A | 3/1997 | Heironimus et al. |
| 5,634,893 | A | 6/1997 | Rishton |
| 6,719,717 | B1 | 4/2004 | Johnson et al. |
| 8,506,512 | B2 | 8/2013 | Aklog et al. |
| 8,734,374 | B2 | 5/2014 | Aklog et al. |
| 11,478,248 | B2 | 10/2022 | Sultan et al. |
| 11,678,905 | B2 | 6/2023 | Look et al. |
| 11,730,499 | B1 | 8/2023 | Thio et al. |
| 11,759,219 | B2 | 9/2023 | Teigen et al. |
| 12,171,917 | B1 | 12/2024 | Buck et al. |
| 12,193,690 | B1 | 1/2025 | Teigen et al. |
| 2001/0049486 | A1 | 12/2001 | Evans et al. |
| 2008/0015485 | A1* | 1/2008 | Sjogren ................. A61M 1/631 |
| | | | 604/4.01 |
| 2009/0163846 | A1 | 6/2009 | Aklog et al. |
| 2011/0213297 | A1 | 9/2011 | Aklog et al. |
| 2011/0301634 | A1 | 12/2011 | Aklog et al. |
| 2012/0165642 | A1 | 6/2012 | Krensky et al. |
| 2013/0304082 | A1 | 11/2013 | Aklog et al. |
| 2015/0173782 | A1 | 6/2015 | Garrison et al. |
| 2016/0151079 | A1 | 6/2016 | Aklog et al. |
| 2016/0151550 | A1 | 6/2016 | Fisher et al. |
| 2016/0303297 | A1 | 10/2016 | Aklog et al. |
| 2017/0035998 | A1 | 2/2017 | Meyering et al. |
| 2017/0043066 | A1 | 2/2017 | Laub |
| 2017/0136158 | A1 | 5/2017 | Culhane et al. |
| 2017/0238953 | A1 | 8/2017 | Yang et al. |
| 2017/0265879 | A1 | 9/2017 | Washburn, II et al. |
| 2018/0014840 | A1 | 1/2018 | Panian |
| 2018/0207397 | A1 | 7/2018 | Look et al. |
| 2018/0353194 | A1 | 12/2018 | Shaffer et al. |
| 2019/0381223 | A1 | 12/2019 | Culbert et al. |
| 2020/0046368 | A1 | 2/2020 | Merritt et al. |
| 2020/0121333 | A1 | 4/2020 | Aklog et al. |
| 2020/0187976 | A1 | 6/2020 | Cartier et al. |
| 2020/0367917 | A1 | 11/2020 | Teigen et al. |
| 2021/0275199 | A1 | 9/2021 | Cote et al. |
| 2022/0240959 | A1 | 8/2022 | Quick |
| 2022/0330960 | A1 | 10/2022 | Buck et al. |
| 2022/0409857 | A1 | 12/2022 | Saadat et al. |
| 2023/0149034 | A1 | 5/2023 | Aklog et al. |
| 2023/0248377 | A1 | 8/2023 | Wainwright et al. |
| 2023/0310751 | A1 | 10/2023 | Merritt et al. |
| 2023/0355259 | A1 | 11/2023 | Marchand et al. |
| 2023/0363883 | A1 | 11/2023 | Merritt et al. |
| 2024/0016505 | A1 | 1/2024 | Horowitz et al. |
| 2024/0074770 | A1 | 3/2024 | Baron et al. |
| 2024/0108366 | A1* | 4/2024 | Horowitz .............. A61M 5/165 |
| 2024/0131235 | A1 | 4/2024 | Horowitz et al. |
| 2024/0148956 | A1 | 5/2024 | Swift et al. |
| 2024/0156473 | A1 | 5/2024 | Aklog et al. |
| 2024/0173042 | A1 | 5/2024 | Yang et al. |
| 2024/0215996 | A1 | 7/2024 | Aklog et al. |
| 2024/0285846 | A1 | 8/2024 | Su et al. |
| 2024/0307166 | A1 | 9/2024 | Merritt et al. |
| 2024/0316258 | A1 | 9/2024 | Horowitz et al. |
| 2024/0358383 | A1 | 10/2024 | Aklog et al. |
| 2024/0366242 | A1 | 11/2024 | Aklog et al. |
| 2024/0407905 | A1 | 12/2024 | Merritt et al. |
| 2025/0064464 | A1 | 2/2025 | Barkley et al. |
| 2025/0064465 | A1 | 2/2025 | Aklog et al. |
| 2025/0099116 | A1 | 3/2025 | Saadat et al. |
| 2025/0127527 | A1 | 4/2025 | Aklog et al. |
| 2025/0143727 | A1 | 5/2025 | Aklog et al. |
| 2025/0143728 | A1 | 5/2025 | Aklog et al. |
| 2025/0143729 | A1 | 5/2025 | Swift et al. |

FOREIGN PATENT DOCUMENTS

| | | |
|---|---|---|
| WO | WO-2006124307 A2 | 11/2006 |
| WO | WO-2019199931 A1 | 10/2019 |
| WO | WO-2022187156 A1 | 9/2022 |

OTHER PUBLICATIONS

FDA Approval Letter dated Mar. 18, 2018 for FDA 510(k) Submission No. K173841, Device Name "AXS Catalyst Distal Access Catheter as part of the AXS Universal Aspiration." Application Dated Dec. 14, 2017, Received Dec. 18, 2017, 24 pages total.

Froehler MT. "Comparison of vacuum pressures and forces generated by different catheters and pumps for aspiration thrombectomy in acute ischemic stroke." Interventional Neurology. Oct. 5, 2017;6(3-4):199-206.

Jaber et al. "Acute pulmonary embolism: with an emphasis on an interventional approach." Journal of the American College of Cardiology. Mar. 2016;67(8):991-1002.

Kohi et al. "Catheter directed interventions for acute deep vein thrombosis." Cardiovascular Diagnosis and Therapy. Dec. 2016;6(6):599-611.

Kucher et al. "Percutaneous catheter thrombectomy device for acute pulmonary embolism: in vitro and in vivo testing." Radiology. Sep. 2005;236(3):852-858.

Liu et al. "Massive pulmonary embolism: treatment with the rotarex thrombectomy system." Cardiovascular and Interventional Radiology. Feb. 2011;34(1):106-113.

Michelson et al. "Use of a modified cardiopulmonary bypass circuit for suction embolectomy with the AngioVac device." The Journal of ExtraCorporeal Technology. Dec. 2017;49(4):299-303.

Non-Final Office Action for U.S. Appl. No. 19/066,822, dated Jul. 23, 2025, 11 pages.

Non-Final Office Action for U.S. Appl. No. 19/230,604, dated Aug. 1, 2025, 16 pages.

Silver et al. "Acute DVT: Are We Overtreating or Undertreating? A look at post-Attract DVT care, necessary next steps, and parameters for future areas of study." Endovascular Today. Jul. 2018;17(7):84-87.

The Penumbra Pivotal Stroke Trial Investigators "The penumbra pivotal stroke trial: safety and effectiveness of a new generation of mechanical devices for clot removal in intracranial large vessel occlusive disease." Stroke. Jul. 9, 2009;40(8):2761-2768.

Todoran et al. "Catheter-based therapies for massive pulmonary embolism." Progress in Cardiovascular Diseases. Mar. 2010;52(5):429-37.

Walsh et al. "Flow changes in the aorta associated with the deployment of a AAA stent graft." Medical Engineering & Physics. May 2003;25(4):299-307.

YouTube video clip entitled "AngioVac Gen 2 Animation." 2 pages, uploaded on Oct. 11, 2017 by user "@AngioDynamicsInc." Retrieved from Internet: <https://www.youtube.com/watch?v=84VytDsalFk>.

YouTube video clip entitled "Medela-Stryker Neurovascular AXS Universal Aspiration System for the treatment of Ischemic strokes." 5 pages, uploaded on Dec. 17, 2018 by user "@MedelaSurgicalCare." Retrieved from Internet: <https://www.youtube.com/watch?v=6d9Y7Jwpeeo>.

* cited by examiner

To suction conduit 264

272

To fluid conduit 252

280

Venting aperture

To vacuum conduit 262

290

230

267

251

From catheter

_410_

402

410

450

403

410

412

420

450

SYSTEMS, DEVICES, AND METHODS INCLUDING FILTERS FOR USE WITH THROMBECTOMY PROCEDURES

CROSS-REFERENCE TO RELATED APPLICATIONS

This application is a divisional of U.S. application Ser. No. 19/066,822, filed Feb. 28, 2025, which claims priority to U.S. Provisional Application No. 63/712,962, filed Oct. 28, 2024.

TECHNICAL FIELD

The embodiments described herein relate generally to systems, devices, and methods for autologous blood transfusion.

BACKGROUND

Thrombosis is the formation of a blood clot inside a blood vessel that may obstruct the flow of blood through the circulatory system. The formation of a thrombus can occur within any artery or vein in the body, leading to a myriad of medical problems such as myocardial infarction, stroke, pulmonary embolism, and deep venous thrombosis. Conventional thrombectomy systems for removing clots from an occluded vessel include mechanical thrombectomy devices for entrapping and dragging clot and vacuum based systems for removing fluid including the clot and blood from the patient. Some existing thrombectomy systems collect and reinject the withdrawn blood back into the patient. The collected fluid may be filtered to remove the clot prior to reinfusion of the aspirated blood. However, existing blood filtering systems are only compatible with syringe based aspiration and require many procedural workflow steps which interfere with the primary therapeutic purpose of clot removal. Additionally, the variations in usage technique of the existing blood filtering systems may cause damage to the blood cells or may allow air to mix with the blood during filtering, which generates unusable blood foam. Excessive blood loss during mechanical thrombectomy can lead to patient complications and may force a physician to terminate the thrombectomy procedure early to avoid the need for a blood transfusion. Therefore, it is desirable to have improved systems, devices, and methods for autologous blood transfusion enabling minimal blood loss during mechanical thrombectomy.

SUMMARY

Described herein are systems, devices, and methods for methods for autologous blood transfusion. In some embodiments, an apparatus may include a fluid conduit configured to receive a volume of fluid from a patient and a container fluidically coupled to the fluid conduit. The container may define a reservoir configured to receive the volume of fluid from the fluid conduit. The apparatus may include a vacuum conduit couplable to a vacuum source, a vent configured to vent air into the reservoir, and at least one valve configured to couple the reservoir to the vacuum conduit to generate negative pressure within the reservoir such that the volume of fluid is drawn into the reservoir, an decouple the reservoir from the vacuum conduit while coupling the reservoir to the vent such that air is vented into the reservoir at an average rate that prevents turbulent movement of the volume of fluid within the reservoir.

In some embodiments, the vent may have a cross-sectional area of between about 0.05 mm$^2$ and about 1.5 mm$^2$. In some embodiments, the container may further include an inlet coupled to the fluid conduit and configured to receive volume of fluid, and a filter disposed within the reservoir downstream from the inlet. The filter may be configured to filter fluid from the volume of fluid that passes through the filter. In some embodiments, the container may further include an outlet port coupled to the reservoir downstream from the filter. The outlet port may be couplable to an extraction device and configured to deliver the fluid filtered by the filter into the extraction device. In some embodiments, the container may include a marking indicating a maximum fluid fill line, and the vent is couplable to the reservoir via a port coupled to the container at a location above the marking to reduce mixing of vented air and the volume of fluid. In some embodiments, the apparatus may comprise a grating disposed within the container upstream of the filter. The grating may be configured to remove a portion of particulates within the volume of fluid.

In some embodiments, the apparatus may include a flow sensor configured to monitor a flow rate of fluid within the fluid conduit. In some embodiments, the flow sensor may include a differential pressure switch, the differential pressure switch configured to detect when a pressure difference between the vacuum conduit and the fluid conduit is greater than a predetermined threshold. In some embodiments, the differential pressure switch may be configured to be disposed at a location that is fluidically upstream from the reservoir by between about 2 feet and about 20 feet. In some embodiments, the apparatus may include an output device configured to generate a user-perceptible signal indicative of a high flow rate in the fluid conduit. The differential pressure switch may be configured to activate the output device to generate the user-perceptible signal when the pressure difference between the vacuum conduit and the fluid conduit is greater than the predetermined threshold.

In some embodiments, the apparatus may include a float valve disposed in the reservoir and configured to prevent fluid within the reservoir from overflowing the reservoir. In some embodiments, the average rate of pressure change is less than about 15 inHg per second. In some embodiments, the volume of fluid includes blood. The apparatus may further include a vacuum regulator configured to maintain the negative pressure within the reservoir higher than a vapor pressure of the blood.

In some embodiments, the volume of fluid may include blood, and the fluid conduit may be coupled between an aspiration catheter disposed in the patient and the container. The fluid conduit may have a cross-sectional area that remains the same or increases in a direction of flow toward the container to avoid a decrease in pressure below a vapor pressure of the blood. In some embodiments, the fluid conduit may have an inner diameter of between about 0.15 inches and about 0.3 inches.

Also described herein is an apparatus including a fluid conduit configured to receive a volume of fluid from a patient, the volume of fluid including a plurality of particulates having different sizes. The apparatus may include a container including an inlet near a first end and an outlet near a second end opposite the first end, the inlet being fluidically coupled to the fluid conduit. The container may define a reservoir configured to receive the volume of fluid from the fluid conduit via the inlet. A first filter may be disposed within the reservoir downstream from the inlet. The first filter may include openings having a first size and being configured to filter particulates from the plurality of particulates having a size greater than the first size. A second filter may be disposed within the reservoir downstream from the first filter and upstream of the outlet. The second filter may be separate from the first filter and disposed near the second end of the container. The second filter may include openings having a second size and being configured to filter particulates from the plurality of particulates having a size greater than the second size. The second size may be smaller than the first size. The outlet may be couplable to a vacuum source that can generate negative pressure to draw at least a portion of the volume of fluid within the reservoir through the second filter and into the vacuum source.

In some embodiments, the volume of fluid may be a first volume of fluid. The outlet may be further configured to receive, before the first volume of fluid is received in the container, a second volume of fluid into the reservoir to fill at least a section of the reservoir disposed downstream of the second filter.

In some embodiments, the volume of fluid may be a first volume of fluid. The outlet may be further configured to receive, before the first volume of fluid is received in the container, a second volume of fluid into the reservoir to submerge the second filter and fill a section of the reservoir disposed downstream of the second filter.

In some embodiments, the second filter may include a two-layer filter or a three-layer filter. In some embodiments, the apparatus may include a vacuum conduit disposed near the first end of the container at a location spaced from the inlet. The vacuum conduit may be configured to generate a negative pressure within the reservoir to draw the volume of fluid into the reservoir.

In some embodiments, the apparatus may include a vent that is couplable to the reservoir via a line that is attached to the container at a location near the first end of the container and spaced from the inlet. The vent, when coupled to the reservoir, may be configured to vent air into the reservoir. In some embodiments, the apparatus may include a flow sensor configured to monitor a flow rate of fluid within the fluid conduit.

Also described herein are methods including the steps of delivering, into a reservoir of a container, a first volume of fluid to fill a space downstream of a filter disposed in the reservoir with the first volume of fluid, coupling a vacuum source to the reservoir such that negative pressure is generated within the reservoir to draw a second volume of fluid into the reservoir via an inlet of the container, coupling, after coupling the vacuum source to the reservoir, a vent to the reservoir to vent air into the reservoir at an average rate that prevents turbulent movement of at least the second volume of fluid, filtering, using one or more filters disposed in the reservoir, at least a portion of the second volume of fluid, and withdrawing, using an extraction device coupled to an outlet of the container, the portion of the second volume of fluid.

In some embodiments, the second volume of fluid may be delivered into the reservoir via a fluid conduit, the method may further include monitoring a flow rate of fluid within the fluid conduit, and in response to detecting that the flow rate is above a predetermined threshold, activating an output device to output a user-perceptible signal.

In some embodiments, the second volume of fluid may be a volume of blood, the volume of blood being received from a patient and containing particulates. The filter may include filtering, using a first filter having openings of a first size, particulates within the volume of blood having a size greater than the first size, and after filtering using the first filter, filtering, using a second filter having openings of a second size, particulates within the volume of blood having a size greater than the second size, the second size being smaller than the first size.

In some embodiments, the method may include decoupling the extracting device from the outlet, and reinfusing, using the extraction device, the portion of the volume of blood back into the patient. In some embodiments, the method may include delivering the first volume of fluid to fill the space downstream of the filter including delivering the first volume of fluid to submerge the filter.

Also described herein are apparatuses including a container couplable to an aspiration catheter via a fluid path, the container defining a reservoir configured to receive fluid aspirated by the aspiration catheter, a vacuum source configured to generate a negative pressure within the container at a pressure level that causes a volume of the fluid to be drawn into the reservoir via the fluid path while avoiding gases dissolved within the volume of the fluid from separating from the fluid, and a vent fluidically coupled to reservoir, the vent configured to vent air into the reservoir at an average rate that avoids turbulent movement of the volume of fluid within the reservoir.

In some embodiments, the vent has a cross-sectional area of between about 0.05 mm$^2$ and about 1.5 mm$^2$. In some embodiments, the average rate of pressure change during venting may be less than about 15 inHg per second. In some embodiments, the fluid may include blood, and the pressure level of the negative pressure may be higher than a vapor pressure of the blood.

In some embodiments, the container may further include an inlet port disposed on or near a top side of the container and configured to receive the fluid, and a filter disposed within the reservoir downstream from the inlet, the filter configured to filter fluid from the fluid that passes through the filter. In some embodiments, the container may further include an outlet port coupled to the reservoir downstream from the filter, the outlet port couplable to an extraction device and configured to deliver the fluid filtered by the filter into the extraction device. In some embodiments, the container may include a marking indicating a maximum fluid fill line. The vent may be couplable to the reservoir via a port coupled to the container at a location above the marking to reduce mixing of vented air and the fluid.

Also described herein are apparatuses including a container including a top end and a bottom end, the container defining a reservoir configured to receive a fluid. An inlet port may be coupled to the top end of the container and configured to deliver fluid that is aspirated by an aspiration catheter into the reservoir. A vacuum port may be couplable to a vacuum source such that the vacuum source can generate negative pressure by removing air within the reservoir to draw the fluid into the reservoir via the inlet port. The vacuum port may be coupled to the container at a height that avoids the fluid drawing into the reservoir from entering the vacuum port. A vent may be coupled to the reservoir at a height that avoids air vented into the reservoir from mixing with the fluid received within the reservoir. A filter may be disposed within the container at a location closer to the bottom end than the top end, the filter being configured to filter the fluid received within the reservoir. An outlet port may be disposed downstream of the filter, the outlet port being couplable to an extraction device and configured to output the fluid into the extraction device.

In some embodiments, the vacuum source may be a first vacuum source, and the extraction device may be a second vacuum source. The outlet port, when coupled to the second vacuum source, may be configured to enable the second vacuum source to generate negative pressure to draw the fluid within the reservoir through the filter and into the second vacuum source.

In some embodiments, the apparatus may include a valve disposed at the vacuum port, the valve configured to be open to allow the negative pressure to be generated within the reservoir to draw the fluid into the reservoir. The valve may be further configured to close to block the vacuum port when the fluid in the reservoir is greater than a predetermined volume to prevent overflow of the fluid from the reservoir into a vacuum conduit coupled to the vacuum port.

In some embodiments, the apparatus may include an overflow tube, the vacuum port being coupled to the vacuum source via a vacuum path that passes through the overflow tube such that the overflow tube can capture any fluid that overflows into the vacuum path.

In some embodiments, the fluid may include blood, and the apparatus may further include a vacuum regulator configured to maintain the negative pressure within the reservoir higher than a vapor pressure of the blood.

Also described herein are systems including an aspiration catheter including a distal end that is configured to be disposed within patient vasculature near clot material, a handle coupled to a proximal end of the aspiration catheter, the handle including an actuator configured to control application of negative pressure to the aspiration catheter to aspirate blood and the clot material into the aspiration catheter. A fluid conduit may be coupled to the handle and configured to receive the blood and the clot material aspirated by the aspiration catheter. A container may be fluidically coupled to the fluid conduit, the container defining a reservoir configured to receive the blood and the clot material from the fluid conduit. A vacuum conduit may be couplable to a vacuum source that is configured to generate negative pressure within the reservoir. The actuator configured to be actuated to fluidically couple the aspiration catheter to the fluid conduit and the container such that the negative pressure within the reservoir can cause the blood and the clot material to be aspirated and drawn proximally along a flow path from the aspiration catheter through the fluid conduit and into the reservoir.

In some embodiments, the actuator may be configured to be actuated to open a valve to establish fluid coupling between the aspiration catheter and the fluid conduit. In some embodiments, the actuator may be a button, and the valve is a pinch valve, and actuator may be configured to be actuated by depressing the button to open the pinch valve. In some embodiments, the actuator may be configured to be released to decouple the aspiration catheter from the fluid conduit and to terminate aspiration of the blood or the clot material. In some embodiments, the actuator, when released, may be configured to close a valve that terminates aspiration of the blood or the clot material.

In some embodiments, the system may include an output device configured to generate a user-perceptible signal indicative of a high flow rate in the fluid conduit, and a flow sensor configured to monitor a flow rate of the blood and the clot material within the fluid conduit, the flow sensor configured to activate the output device based on the monitored flow rate.

In some embodiments, the system may include the vacuum source, the vacuum source configured to provide continuous negative pressure, a valve configured to isolate the reservoir from the vacuum source, and a vent configured to allow air to enter the reservoir to bring pressure within the reservoir back to atmospheric pressure after the reservoir is isolated from the vacuum source.

Also described herein are apparatuses including a fluid conduit configured to receive a volume of fluid from a patient, a vacuum conduit couplable to a vacuum source configured to generate a vacuum pressure to draw the volume of fluid into a reservoir, an output device configured to output a user-perceptible signal indicative of a high flow rate in the fluid conduit, and a flow rate sensor coupled to the fluid conduit. The flow sensor may be configured to detect when a flow rate of the fluid within the fluid conduit is greater than a predetermined threshold, and activate the output device to output the user-perceptible signal in response to detecting that the flow rate is greater than the predetermined threshold.

In some embodiments, the flow rate sensor may be a differential pressure switch coupled to the fluid conduit and the vacuum conduit, the differential pressure switch being configured to be disposed at a location that is fluidically upstream from the reservoir by between about 2 feet and about 20 feet.

In some embodiments, the differential pressure switch may include a flow-through flow path disposed inline with the fluid conduit and a port coupled to the vacuum conduit via fluid line. In some embodiments, the user-perceptible signal may be an audible signal. In some embodiments, the reservoir may be configured to receive the volume of fluid, the reservoir being couplable to the fluid conduit and the vacuum conduit such that vacuum pressure generated within the vacuum conduit can generate negative pressure within the reservoir to draw the volume of fluid into the reservoir.

In some embodiments, a vent may be configured to vent air into the reservoir. The reservoir may be selectively couplable to one of the vacuum conduit or the vent. The apparatus may include a filter disposed within the reservoir. The filter may be configured to filter fluid from the volume of fluid that passes through the filter. An outlet port may be coupled to the reservoir downstream from the filter. The outlet port may be couplable to an extraction device and configured to deliver the fluid filtered by the filter into the extraction device.

In some embodiments, the predetermined threshold may be a first predetermined threshold, and the user-perceptible signal may be a first user-perceptible signal. The fluid conduit may be coupled to an aspiration catheter that is configured to aspirate the volume of fluid while ingesting a clot from the patient. The output device may be configured to output a second user-perceptible signal indicative of the clot being ingested. The flow rate sensor may be configured to cause the output device to output the second user-perceptible signal in response to detecting that the flow rate is greater than the second predetermined threshold and less than the first predetermined threshold.

Also described herein are apparatuses including a fluid conduit configured to receive a volume of fluid from a patient, the volume of fluid including a plurality of particulates. A container may include an inlet near a first end and an outlet near a second end opposite the first end, the inlet being fluidically coupled to the fluid conduit, the container defining a reservoir configured to receive the volume of fluid from the fluid conduit via the inlet, and the output being couplable to an extraction device. A vacuum conduit may be couplable to a vacuum source that is configured to generate a negative pressure within the reservoir to draw the volume of fluid into the reservoir. A filter may be disposed within the reservoir downstream from the inlet and upstream of the outlet, the filter disposed near the second end of the container, the filter being configured to filter the plurality of particulates from the volume of fluid. A port may be coupled to the container and configured to receive air into the container to generate a positive pressure within the reservoir to drive the volume of fluid through the filter such that the plurality of particulates are filtered from the volume of fluid and to output at least a portion of the volume of fluid into the extraction device when the extraction device is coupled to the output.

In some embodiments, the volume of fluid may be a first volume of fluid. The outlet may be further configured to receive, before the first volume of fluid is received in the container, a second volume of fluid into the reservoir to fill at least a section of the reservoir disposed downstream of the filter. In some embodiments, the filter may include a two-layer filter or a three-layer filter. In some embodiments, the apparatus may include a vent that is couplable to the reservoir via the vacuum conduit. The vent, when coupled to the reservoir, may be configured to vent air into the reservoir.

In some embodiments, the apparatus may include a flow sensor configured to monitor a flow rate of fluid within the fluid conduit. In some embodiments, the filter may be a fine filter, the apparatus may further include a coarse filter disposed within the reservoir downstream from the inlet and upstream of the fine filter. The coarse filter may include openings having a first size and being configured to filter particulates having a size greater than the first size. The fine filter may include openings having a second size and being configured to filter particulates having a size greater than the second size, the second size being smaller than the first size. In some embodiments, the vacuum conduit may be couplable to the reservoir via the port and configured to deliver the air into the container via the port to generate the positive pressure.

DETAILED DESCRIPTION

Figure 1:
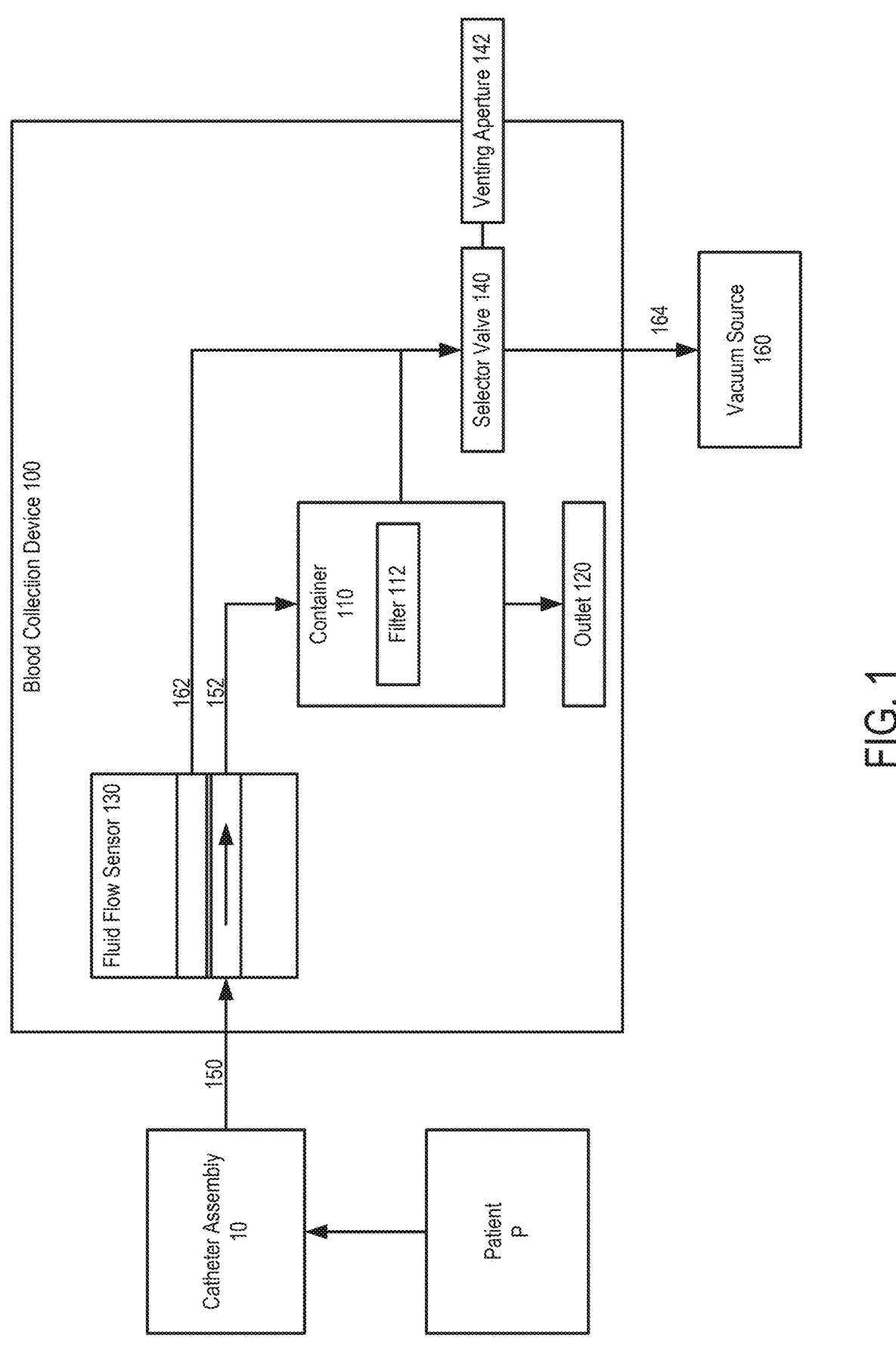
FIG. 1 is a schematic diagram of a blood collection system, according to embodiments.

Described herein are systems, devices, and methods for autologous blood transfusion by removing and filtering blood from a vessel of a subject while minimizing hemolysis, blood cell damage, and foaming. Systems and devices described herein can include a blood collection device (e.g., a blood collection reservoir) configured to recover and prepare blood for reinjection into the subject. In some embodiments, systems, devices, and methods described herein can be used with a catheter assembly (e.g., thrombectomy device) configured to remove a thrombus from a patient. In some embodiments, the catheter assembly and blood collection device may be coupled to a vacuum source such as a continuous vacuum source (e.g., a vacuum pump). The systems and devices described herein may be designed to recover and filter the blood (e.g., remove the thrombus) while minimizing hemolysis, blood cell damage, and/or foaming, thereby enabling autologous blood transfusion of undamaged blood resulting in minimal or reduced blood loss and improved thrombectomy outcomes. In some embodiments, blood from a subject may be received by a blood collection device using continuous negative pressure. A continuous vacuum source provides advantages over syringe-based vacuum sources because the negative pressure decays as a syringe fills with aspirated fluid. Additionally, syringe-based vacuum sources require many steps to empty the syringe and pull vacuum on the syringe plunger each time fluid is aspirated. By contrast, a continuous vacuum source (e.g., suction pump) maintains maximum or sustained vacuum pressure throughout a procedure and can be used to aspirate fluids without interruption. The received fluid (e.g., blood with saline and clot) is collected in the blood collection device. Importantly, a continuous vacuum source requires a shut off valve at some location between the vacuum source and the thrombectomy catheter and/or requires active control of the vacuum source to shut off operation of the vacuum source. In some embodiments, a continuous vacuum source may be used with a thrombectomy catheter (e.g., aspiration catheter) having an incorporated valve configured to shut off or decouple the vacuum source from the thrombectomy catheter. For example, systems and devices described herein can include a shut off valve between the continuous vacuum source and the blood collection device and can be configured to be used with a thrombectomy catheter that incorporates an integrated activation valve. This allows for fluidic isolation of the blood collection device from both the continuous vacuum source and the patient blood pressure.

In some embodiments, the blood collection device includes features to enable removal of trapped air. Trapped air can expand rapidly when a vacuum source is fluidically connected, and the rapid movement of blood resulting from the expansion can cause damage to blood cells. Rapid venting of vacuum pressure to atmospheric pressure can also be damaging to blood cells. As such, it can be desirable to vent blood received into the blood collection device to atmospheric pressure at a predetermined rate that does not cause rapid movement of blood, e.g., to reduce hemolysis, blood cell damage, and/or foaming. In some embodiments, the rate of venting from vacuum pressure to atmospheric pressure can be at an average rate of pressure change less than about 15 inHg per second, inclusive of subranges or values therebetween, including, for example, about 14 inHg per second. In some embodiments, the rate of venting from vacuum pressure to atmospheric pressure can be less than a maximum rate of about 50 inHg per second, inclusive of subranges and values therebetween. In some embodiments, the venting from vacuum pressure of the blood collection device to atmospheric pressure can be over a predetermined period of time, such as, for example, over at least about 2 seconds of vent time, inclusive of subranges and values therebetween. In some embodiments, the vent rate can be controlled by first isolating the blood collection device from the continuous vacuum source, and then allowing atmospheric air to enter the blood collection device through an aperture (or apertures) with a cross-sectional area between about 0.05 $mm^2$ and about 2 $mm^2$ to achieve the target venting rate, inclusive of all subranges and values therebetween. In some embodiments, the blood collection device may incorporate a flow sensing element to provide the user feedback about the rate of blood and thrombus being removed from the patient. In some embodiments, the blood collection device can incorporate one of more filters to separate ingested clot from the blood. The blood collection device may further be disposed within the sterile field, e.g., to maintain sterility of the blood and to improve ergonomics.

In some embodiments, systems, devices, and methods described herein can be used to remove fluid (e.g., thrombus, embolus, blood clot, blood) from a patient and filter the fluid for blood transfusion back into the subject. The blood collection device may be coupled to a catheter assembly such as a thrombectomy device. Suitable examples of such catheter assemblies and systems are described in International Application Serial No. PCT/US2019/026737, filed on Apr. 10, 2019, and titled "HYDRODYNAMIC VORTEX ASPIRATION CATHETER," International Application Serial No. PCT/US2022/018182, filed on Feb. 28, 2022, and titled "ASPIRATION DEVICES FOR TREATMENT OF THROMBOSIS INCLUDING EXPANDABLE DISTAL ENDS AND SYSTEMS AND METHODS THEREOF," and U.S. application Ser. No. 18/241,588, filed on Sep. 1, 2023, and titled "SYSTEMS, DEVICES, AND METHODS FOR ASPIRATION, INCLUDING EXPANDABLE STRUCTURES AND ROTATABLE SHAFTS," the disclosure of each of which is hereby incorporated by reference in its entirety.

I. System

Systems and devices described herein can be configured to remove and process fluids from vasculature, including, for example, a thrombus and blood. Systems and devices described herein can include a catheter assembly, a blood collection device, and a vacuum source, as depicted in FIG. 1. FIG. 1 is a schematic block diagram of a thrombectomy system or aspiration catheter system including a catheter assembly 10 in fluid communication with a blood collection device 100 and a vacuum source 160. In embodiments, the catheter assembly 10 can include an integrated valve, as further described below. The blood collection device 100 may be coupled between the catheter assembly 10 and the vacuum source 160. Generally, the blood collection device 100 may include a container 110, an outlet 120 (e.g., port), a flow sensor 130, a fluid conduit 150, a selector valve 140, a venting aperture 142 (e.g., vent), and a vacuum conduit 162. The container 110 can define a reservoir configured to receive a volume of fluid. The fluid conduit 150 may be coupled to the container 110 via an inlet or inlet port disposed on or near a top side of the container 110 and configured to deliver and/or receive the fluid that is aspirated by an aspiration catheter into the reservoir. The vacuum source 160 may be configured to supply a negative pressure to a suction port of the catheter assembly 10, the container 110, and the vacuum conduit 162 coupled to the flow sensor 130 and the suction portion of the catheter assembly 10. For example, the vacuum source 160, when coupled to the container 110 via the vacuum conduit 162, may be configured to generate a vacuum pressure to draw a volume of fluid into a container 110 (e.g., reservoir) via the fluid conduit 150. The container 110 may be configured to receive the volume of fluid. The container 110 may be couplable to the fluid conduit 150 and the vacuum conduit 162 such that vacuum pressure generated within the vacuum conduit 162 can generate negative pressure within the container 110 to draw the volume of fluid from the fluid conduit 150 into the container 110.

The venting aperture 142 may be selectively couplable to the container 110, e.g., via a line that is attached to the container 110 at a location near a first end (e.g., top side, top end) of the container and spaced from an inlet (e.g., inlet port) of the container 110. In some embodiments, the venting aperture 142 can be coupled to the container 110 via the vacuum conduit 162. In such embodiments, a selector valve 140 can selectively couple the venting aperture 142 to the vacuum conduit 162 while decoupling the vacuum source 160 from the vacuum conduit 162. The venting aperture 142, when coupled to the container 110, may be configured to vent air into the container 110.

In some embodiments, the catheter assembly 10 may have a catheter (e.g., aspiration catheter) having a distal end disposed in a body cavity or lumen (e.g., pulmonary artery) of a patient P. In some embodiments, the catheter assembly 10 can include a port or fitting couplable to a vacuum source 160 via blood collection device 100. The catheter assembly 10 can include a valve that is configured to open or close a fluid path that connects the catheter assembly 10 to the blood collection device 100, which in turn is coupled via the fluid path to the vacuum source 160. In some embodiments, the distal end of the catheter may be configured to ingest a clot by negative pressure generated by the vacuum source 160. The catheter assembly 10 can include one or more actuators (e.g., buttons, sliders, etc.), which can be actuated by a user to open the valve, such that negative pressure can be supplied to the lumen of the catheter of the catheter assembly 10, thereby drawing in fluids and/or clot into the distal end of the catheter.

In some embodiments, the catheter assembly 10 can be similar to catheter systems and devices described in International Application Serial No. PCT/US2019/026737, International Application Serial No. PCT/US2022/018182, or U.S. application Ser. No. 18/241,588, incorporated above by reference. For example, the catheter assembly 10 can include a distal end having an expandable structure or tip. In some embodiments, the expandable tip in the expanded configuration may have a generally funnel-shaped profile that gradually increases in diameter from a proximal end of the expandable tip to a distal end of the expandable tip. The expandable structure can be configured to expand such that a thrombus or clot can be proximally drawn into the expandable structure. In some embodiments, a sheath or outer sleeve can be disposed over the expandable structure. Movement of the sheath or catheter relative to the other can then allow the expandable structure to expand. In some embodiments, the catheter assembly 10 can also include a shaft or other macerating element, which can be configured to break, fragment, and/or reshape the thrombus or clot when it drawn into the expandable structure. Blood and/or other fluid carrying the broken, fragmented, and/or reshaped thrombus or clot can then be transported, via the catheter of the catheter assembly 10, to the blood collection device 110.

When the vacuum source 160 is used to apply negative pressure to suction blood and clot out of patient anatomy, it is important to monitor blood flow and to limit blood loss through the catheter. For example, it can be desirable to limit blood loss to amounts less than about 250 ml. To facilitate this, one or more sensing elements (e.g., sensor 130) can be used to monitor one or more parameters associated with fluid flow from the catheter, including, for example, fluid flow rate, pressure, volume, and/or changes thereof.

In some embodiments, the catheter assembly 10 may be coupled to the blood collection device 100 via the fluid conduit 150. For example, the fluid conduit 150 may be configured to receive a volume of fluid from a patient via the catheter assembly 10. A sensor such as flow sensor 130 may be coupled to the fluid conduit 150 and configured to detect changes in a flow rate of the fluid in the fluid conduit 150. Measurements of the fluid flow rate, pressure, or other parameters associated with the fluid flow within fluid conduit 150 can be indicative or representative of such parameters within the catheter assembly 10, which in turn can be indicative of clot engagement, ingestion, etc. For example, the fluid flow rate through fluid conduit 150 may be relatively low when a clot is being captured (e.g., ingested) by the catheter assembly 10. In such instances, it can be desirable to continue application of negative pressure to the catheter assembly 10 such that the clot can continue to be ingested into the catheter assembly 10. In some embodiments, as described above, the catheter assembly 10 can include a shaft or other agitation element, which can be configured to break or reshape the thrombus or clot over time. Therefore, further application of negative pressure to the catheter assembly 10 can be desirable to continue pulling or drawing clot into the catheter assembly 10 while the clot is being broken or reshaped. In some embodiments, the catheter assembly 10 can include one or more openings near a distal end of the catheter, which can be configured to provide a minimal or small amount of fluid flow (e.g., via blood drawn into the catheter via the openings) to continue proximal ingestion and transport of the clot, even if the distal end of the catheter becomes blocked (or substantially blocked) by the clot. This mixing of a small amount of fluid with the ingested clot also prevents a large clot from filling the catheter assembly 10 primarily with solid clot material which can cause the catheter assembly 10 to become clogged.

When a clot is not being drawn into the catheter assembly 10, the fluid flow rate through the fluid conduit 150 may be relatively high. For example, if the catheter assembly 10 is not disposed sufficiently close to a clot, or as the catheter assembly 10 finishes removing a clot, the flow rate can increase due to the lower resistance of blood travelling through the catheter assembly 10 relative to an obstruction such as a clot. Therefore, further aspiration of blood at such higher fluid flow rates can quickly lead to significant volumes of blood being removed from a patient. It can be undesirable to continue application of vacuum pressure in these instances, as it would lead to excess blood loss while not contributing to removal of clot material. Therefore, in some embodiments, it can be desirable to have a sensing element that is configured to monitor the flow rate of fluids within the fluid conduit 150.

In some embodiments, a flow sensor 130 can be configured to detect when there is an increase in the flow rate of the fluid in the fluid conduit 150. For example, when the flow sensor 130 detects that the flow rate increases (e.g., indicating lack of ingestion and/or transport of clot material), a user-perceptible signal, alert, or other indication can be provided to a user. For example, the flow sensor 130 can be operatively coupled to one or more indicators or output devices (e.g., audible signal, visual or light indicators) or be configured to activate one or more output devices such that when the flow sensor 130 detects a predetermined flow rate or a predetermined change in flow rate, the output device can alert a user and signify to the user to terminate or pause further operation of the catheter assembly 10. The user can then terminate or pause further operation of the catheter assembly 10 by, for example, releasing the actuator (e.g., button, slider, etc.) to close the valve along the flow path that couples the vacuum source 160 to the catheter assembly 10. In some embodiments, the flow sensor 130 can be configured detect when the flow rate is greater than a predetermined threshold, when the flow rate is within a predetermined range of flow rates, when a change in the flow rate is greater than a predetermined threshold, or when one or more other parameters (or changes in other parameters) indicative of a change in flow rate are greater than or less than a predetermined threshold or are outside of a predetermined range. For example, the flow sensor 130 can be configured to detect pressure within the fluid conduit 150, e.g., via an absolute measurement or a relative measurement of pressure within the fluid conduit 150 compared to a vacuum line or reference. Pressure within the fluid conduit 150 can be relatively high when a clot is being captured (e.g., ingested) or transported by the catheter assembly 10, whereas pressure within the fluid conduit 150 can be relatively low when a clot is not being drawn within the catheter assembly 10. Therefore, the flow sensor 130, by monitoring the pressure within the fluid conduit 150, can be configured to monitor when there is clot being ingested and drawn proximally within the catheter assembly 10 and when there is no clot being ingested or drawn proximally within the catheter assembly 10.

As shown in FIG. 1, the fluid conduit 150 can be coupled to the flow sensor 130, which in turn can be coupled to additional tubing or a fluid conduit 152, which carries the blood and particulates having different sizes from the patient P to the container 110. While two fluid conduits are described, it can be appreciated that any number of tubing, conduits, etc. can be coupled together to provide a fluid path from the catheter assembly 10 to the container 110. In embodiments described herein, the fluid flow sensor 130 can be disposed along this fluid path.

In some embodiments where a pressure within the fluid conduit 150 is being monitored relative to a vacuum reference or a vacuum line, it is necessary to sufficiently space the location where the pressure measurement associated with the fluid conduit 150 is taken from the source of the vacuum pressure. For example, if the pressure associated with the fluid conduit 150 were to be closely positioned relative to the source of vacuum pressure, then that source would dictate the pressure being measured and no difference in pressure between the fluid conduit 150 and the vacuum reference may be detected. The pressure within the vacuum conduit and vacuum source is substantially equal throughout. Therefore, in embodiments described herein, a predetermined distance or length of tubing or line (e.g., fluid conduit 152) may be used to separate the point at which pressure associated with the fluid conduit 150 is being measured from the point at which the vacuum pressure is coupled to the blood collection device 100. In some embodiments, the predetermined length of tubing from which the pressure is measured along the fluid conduit to the container can be at least about 2 feet, at least about 3 feet, at least about 4 feet, at least about 5 feet, at least about 6 feet, at least about 7 feet, at least about 10 feet of tubing, at least about 12 feet, at least about 14 feet, at least about 16 feet, at least about 18 feet, at least about 20, between about 2 feet and about 20 feet, between about 2 feet and about 10 feet, between about 5 feet and about 15 feet, between about 10 feet and about 15 feet, and between about 10 feet and about 20 feet, inclusive of all subranges and values therebetween.

In some embodiments, the flow sensor 130 can be coupled to a controller (e.g., a processor or other processing circuitry), which can be configured to shut off the vacuum source 160 or decouple the supply of vacuum pressure to the catheter assembly 10 (e.g., using a shut off valve or selector valve) when the flow sensor 130 detects a change in the flow rate or a parameter associated with the flow rate. In some embodiments, systems and devices described herein can be configured to monitor a state of clot travel or movement through the catheter assembly 10 and into the blood collection device 100. For example, a controller coupled to a sensing element (e.g., flow sensor 130) can be configured to monitor changes in flow rate, pressure, and/or another parameter within the fluid conduit 150. The controller can be configured to determine, based on monitoring the changes in flow rate, pressure or another parameter within the fluid conduit 150, one or more states of the clot. For example, the controller can be configured to determine based on the monitoring whether a clot is being engaged by the catheter assembly 10 (e.g., being engaged by the distal end of the catheter of the catheter assembly 10), being ingested by the catheter assembly 10, and/or being transported or drawn proximally within the catheter assembly 10. When the clot is initially being engaged by the catheter assembly 10, the controller may detect that the fluid flow rate goes from relatively high to little or minimal flow; when the clot is being ingested by the catheter assembly 10, the controller may detect that the fluid flow rate goes from relatively little or minimal flow to slightly higher but still relatively lower flow; and when the clot has been ingested and is being proximally withdrawn or transported via the catheter assembly 10, the controller may detect that the fluid flow rate goes from relative lower flow to relatively higher flow. Therefore, by monitoring changes in the flow rate (or another parameter associated with or indicative of the flow rate), systems and devices described herein can be configured to track a state of the clot movement as the clot is engaged, ingested, and transported within the catheter assembly 10 to the blood collection device 100.

In some embodiments, systems and devices described herein can be configured to monitor an average flow rate, or other parameter averaged over a predetermined period of time (e.g., between about 1 second and 5 seconds, including subranges and values therebetween). Monitoring an average flow rate or other parameter can be beneficial, e.g., to avoid spikes or short changes in the flow rate or parameter from causing an alert or impacting the application of vacuum pressure.

While systems and devices disclosed herein have been described as being configured to monitor when fluid flow rate is relatively high (and therefore indicative of fluid flow without clot ingestion), it can be appreciated that one or more other situations or conditions can be monitored. For example, systems and devices disclosed herein can be configured to monitor when fluid flow rate is below a predetermined threshold, or when pressures are above a predetermined threshold, to alert a user (e.g., via an output device using a user-perceptible signal) to a catheter that may have become blocked. For example, for an aspiration catheter without an agitator, it can be desirable to monitor when that aspiration catheter has become blocked by clot material. Therefore, by monitoring when pressures are relatively high, when fluid flow rate is relatively low, or when another parameter meets a certain criterion, systems and devices can alert a user as to a blockage. The user, upon receiving the alert, can then release an actuator to decouple the vacuum source from the catheter and/or shut off the vacuum source. In some embodiments, systems and devices disclosed herein can be configured to output (e.g., via an output device) different information to indicate to a user when a clot is being engaged, when a clot is being ingested, and/or when a clot is being transported or proximally withdrawn within a catheter (e.g., of the catheter assembly 10). For example, systems and devices disclosed herein can be configured to output a first sound to indicate that a clot has been engaged, to output a second and different sound when a clot is being ingested, and to output a third and different sound when a clot is being drawn proximally within the catheter. Alternatively or additionally, systems and devices disclosed herein can be configured to output different visual signals (e.g., different colored lights or flashes of light) to indicate the different states of clot removal.

In some embodiments, the flow sensor 130 may be implemented as a differential pressure flow sensor or differential pressure switch configured to detect a difference in pressure between the fluid conduit 150 and a vacuum reference. The vacuum reference can be provided via a second conduit, e.g., vacuum conduit 162 couplable to a vacuum source 160. In some embodiments, the differential pressure switch may include a flow-through flow path disposed inline with the fluid conduit 150 and a port coupled to the vacuum conduit 162 via a fluid line. For example, the switch can include a membrane or other movable component that is disposed between a first fluid path being the path that is coupled to the catheter assembly 10 (e.g., the fluid conduit 150) and a second fluid path being a path that is coupled to the vacuum source 160 (e.g., a suction conduit 162). The switch can then monitor changes in pressure between the two fluid paths and thereby monitor a flow rate of fluid within the fluid conduit 150. In particular, the membrane or movable component of the switch can be configured to change state based on the pressure in the two fluid paths. The differential pressure switch (or other flow sensor) may be configured to activate the output device to generate the user-perceptible signal when the pressure difference between the vacuum conduit 162 and the fluid conduit 150 (corresponding to the flow rate of fluid within the fluid conduit) is greater than a predetermined threshold. For example, when the pressure in the fluid path coupled to the catheter assembly 10 (e.g., the fluid conduit 150) is lower (similar to the pressure in the vacuum conduit 162), e.g., indicative of there being a clot being ingested or captured by the catheter assembly 10, then the membrane can have a first configuration (e.g., an off configuration or off state) that does not trigger an output device. When the pressure in the fluid path coupled to the catheter assembly 10 (e.g., the fluid conduit 150) is greater than the pressure in the vacuum conduit, e.g., indicative of higher fluid flow in the fluid conduit and therefore no digestion of clot material, then the membrane can transition to a second configuration (e.g., an on configuration or on state). In the second configuration, the switch 140 can activate an indicator or output device, such as an audio device, display, light, etc., to output a first user-perceptible signal indicative of a high flow rate in the fluid conduit 150. In some embodiments, the blood collection device can be configured to indicate different states of clot removal to a user. For example, when the pressure in the fluid path is greater than the vacuum pressure by a first predetermined amount indicative of fast flow, then the differential pressure sensor can be configured to activate a first indicator (e.g., a first sound or a first light). When the pressure in the fluid path coupled to the catheter assembly 10 (e.g., the fluid conduit 150) is greater than the vacuum pressure by a second predetermined amount but less than the first predetermined amount (e.g., indicating that there may be some clot being aspirated through the aspiration catheter and fluid conduit 150), then the differential pressure sensor can be configured to activate a second indicator (e.g., a second sound or a second light). As described above, the differential pressure switch may be configured to be disposed at a location that is fluidically upstream from the container 110 (e.g., reservoir) of the blood collection device by between about 2 feet and about 20 feet, inclusive of subranges or values therebetween.

In embodiments, it can be desirable to provide the indication of fast flow to a user, such as an physician, without automatically shutting off the vacuum driven flow (e.g., without decoupling the aspiration catheter form the vacuum source). This can allow a physician to control when to decouple the aspiration catheter from the vacuum source. This can be advantageous to a physician, as a physician may want to continue flow under certain circumstances, e.g., to ensure that a clot has been fully removed.

Alternatively or additionally, the flow sensor 130 can be implemented as a thermal flow sensor (e.g., configured to measure conduction of heat to determine flow rate), ultrasonic flow sensor, electromagnetic flow sensor, force or displacement based flow sensor (e.g., configured to measure forces acting on a target or displacement of a target to determine flow rate), a turbine based flow sensor, a magnetic induction flow sensor, or capacitive flow sensor or the like. In some embodiments, the flow sensor 130 may be coupled to the fluid conduit 150 without being coupled to the vacuum conduit 162.

In some embodiments, fluid from the catheter assembly 10 (carried by the fluid conduits 150, 152) may be stored and filtered using a container 110. The container 110 may be configured to receive the fluid (e.g., blood and thrombus) from the fluid conduit 152. The container 110 may include an inlet or inlet port at or near a first side or a first end (e.g., a top side) that is couplable to the fluid conduit 152. As described above, the container 110 can also include an outlet or outlet port 120 that is at or near a second side or second end (e.g., a bottom side) of the container 110. The container 110 defining a reservoir may be configured to receive the fluid from the fluid conduit 152 via the inlet. In some embodiments, the vacuum conduit 162 may be coupled to the container 110 near the first end of the container 110, e.g., at a location spaced from the inlet and/or with a shield between the inlet and the coupling point of the vacuum conduit 162 (e.g., to avoid fluids (e.g., blood) entering the reservoir via the inlet from entering the vacuum conduit 162). Additionally, the vacuum conduit 162 can be coupled to the container at a height that avoids fluid within the container (e.g., blood) from being drawn into the vacuum conduit 162. For example, the vacuum port may be located above a maximum fill line of the container.

In some embodiments, the fluid stored in the container 110 may be received under vacuum and brought to atmospheric pressure within the container 110 at a predetermined rate, e.g., to facilitate blood transfusion and reduce hemolysis and blood cell damage. In some embodiments, the container 110 can include a filter 112. The filter 112 may be disposed within the reservoir downstream from the inlet of the container. The filter 112 may be configured to filter fluid from the volume of fluid that passes through the filter. For example, the filter 112 can filter blood containing particulates (e.g., clot, thrombus). The filter can be disposed at a point along a longitudinal axis of the container 110, and can separate a first region or volume of the container from a second region or volume of the container. In some embodiments, the filter 112 can be disposed closer to a bottom end (e.g., second side or second end) of the container 110 than a top end (e.g., first side or first end). As blood passes through the filter 112 (e.g., from the first region to the second region), the blood is filtered. In some embodiments, the filtered blood can be suitable for transfusion (e.g., blood not including air pockets, without blood foam, and without particulates). In some embodiments, the filtered blood can be used for blood sampling or testing. In some embodiments, the filtered blood can be removed from the container via an outlet 120 (e.g., outlet port), which is coupled to the container 110 at a location that is downstream from the filter 112. In other words, the outlet 120 can be coupled to the container 110 at a location distal to the filter 112, thereby ensuring that blood received at the outlet 120 has been filtered (e.g., does not include particulates). The outlet 120 may be couplable to an extraction device (e.g., syringe, another vacuum source, not shown in FIG. 1) and configured to deliver the fluid filtered by the filter 112 into the extraction device. For example, the extraction device coupled to the outlet 120 may be configured to generate negative pressure to draw fluid within the reservoir through the filter and into the extraction device. In some embodiments, the outlet 120 can include an extraction tube and fitting. A standard syringe may be connected to the fitting on the extraction line and as blood is drawn into the syringe, blood flows from the first region of the container 110, through the filter, into the second region of the container 110, and then out through the extraction tube. Utilizing negative pressure generated in the extraction syringe to draw the blood through the filter limits the flow rate and reduces hemolysis and blood cell damage. In use, the filter 112 can be fully submerged in a fluid (e.g., saline or another priming fluid, intravenous fluid, etc.) before using the blood collection device 100 to collect blood from a patient. This prevents any air mixing with the blood as the blood moves across the filter 112. The fully submerged filter 112 can minimize or reduce blood foaming, hemolysis, and/or blood cell damage. In embodiments, the syringe can then be used to deliver blood for blood sampling and/or testing, or to deliver blood to a container, catheter, sheath, etc. for reinfusion of blood back into patient anatomy. For example, the syringe can be coupled to a port or other fitting of a catheter or sheath (e.g., a sheath of the catheter assembly 10) to reintroduce the blood into the patient vasculature.

In some embodiments, the filter 112 can be a fine filter and a coarse filter or a grating (not depicted in FIG. 1) can also be disposed in the container 110. For example, the fine filter may be disposed within the container 110 downstream from an inlet of the container 110 and upstream of an outlet of the container 110. The fine filter may be disposed near a second end (e.g., bottom end, bottom side) of the container 110. The coarse filter may be disposed within the container 110 downstream from the inlet and upstream of the fine filter. The coarse filter may include openings having a first size and may be configured to filter particulates having a size greater than the first size. The fine filter may include openings having a second size and may be configured to filter particulates having a size greater than the second size where the second size is smaller than the first size. In some embodiments, the coarse filter can be supported on or form part of an inlet assembly, which can include the inlet that is couplable to the fluid conduit 152 and a catch container (e.g., a container, can, tray, etc.). The catch container can include the coarse filter. In some embodiments, the inlet assembly can be removed from or decoupled from the container 110. As such, a physician may remove the inlet assembly during a procedure to visually examine whether larger clot or thrombus has been effectively ingested by the aspiration catheter and captured in the blood collection device 110. The inlet assembly can be coupled to the container 110 via a screw fit, friction fit, or other mechanical fit.

As described above, the vacuum source 160 or the amount of vacuum applied catheter assembly 10 may be controlled using an actuator or switch (not shown), e.g., to control an amount of vacuum pressure being applied through the catheter assembly 10. In some embodiments, the actuator may include a valve and/or activation element configured for manual control of continuous and/or discrete levels of negative suction. For example, the actuator be disposed within or on a handle coupled to a proximal end of the catheter assembly 10. The user can actuate the actuator to apply negative pressure to the catheter assembly 10 and can release it to reduce or shut off vacuum within the catheter assembly 10. The user can also use the actuator to generate pulsed suction and/or metered flow. For example, the actuator may be configured to be actuated to open a valve to establish fluid coupling between the aspiration catheter and the fluid conduit. Conversely, the actuator may be configured to be released to decouple the aspiration catheter from the fluid conduit and to terminate aspiration of the blood or the clot material. The actuator, when released, may be configured to automatically transition to a closed state to close the valve to terminate aspiration of the blood or the clot material. In some embodiments, the vacuum source 160 can be electronically and/or mechanically controlled such that the vacuum source 160 can automatically shut off or reduce the vacuum within the catheter assembly 110, e.g., when a fluid flow rate is above a predetermined threshold. In some embodiments, a controller (e.g., processor) can be configured to turn off and/or off the vacuum, while in other embodiments, the controller can be configured to adjust an amount of the vacuum pressure (e.g., among one or more values). In some embodiments, the actuator may include a button, and the valve may be a pinch valve such that the actuator may be configured to be actuated by depressing the button to open the pinch valve.

In some embodiments, the vacuum source 160 can be separately disposed from the blood collection device 100, e.g., outside of a housing of the blood collection device 100, and therefore be coupled to the blood collection device via tubing or a conduit 164. In other embodiments, the vacuum source 160 can be integrated into the blood collection device 100, e.g., disposed within a housing of the blood collection device 100. In some embodiments, the blood collection device 100 may be configured to maintain the negative pressure within the reservoir higher than a vapor pressure of the blood in order to prevent the release of gases from blood (e.g., a volume of fluid) within the container. Optionally, the blood collection device 100 can include a component for regulating the pressure level within the container 110. For example, the container 110 can be coupled to a valve and/or vent, which can be configured to allow air to pass into the container when the pressure level within the container is less than a predetermined threshold (e.g., less than a vapor pressure of the blood).

The blood collection device 100 can also include a selector valve 140, which can be configured to selectively switch between coupling the container 110 (and components coupled thereto, including, for example, the fluid conduits 150, 152 and the catheter assembly 10) and vacuum conduit

162 to (1) the vacuum source 160 or (2) a venting aperture, vent, or opening 142. For example, the valve 140 may be configured to (1) couple the reservoir to the vacuum conduit to generate negative pressure within the reservoir such that the volume of fluid is drawn into the reservoir or (2) decouple the reservoir from the vacuum conduit while coupling the reservoir to the vent such that air is vented into the reservoir at an average rate that prevents turbulent movement of the volume of fluid within the reservoir. It may be necessary to switch between coupling to the vacuum source 160 or a venting aperture 142 so that pressures within the container 110 can be equalized with pressure within a syringe (e.g., for removing blood from container 110) or be brought closer to atmospheric pressure to enable removal of blood from the container 110. Therefore, a selector valve 140 can be configured to be switched between two positions or configurations, e.g., to selectively couple the vacuum source 160 or the venting aperture 142 to the container 110, the catheter assembly 10, and/or other components of the blood collection device 100. The selector valve 140 can be switched between its two configurations manually and/or electronically, e.g., by a user. For example, the selector valve 140 can be coupled to a switch or other actuator, which can be actuated by a user to selectively couple the vacuum source 160 or the venting aperture 142 to the container 110, the catheter assembly 10, and/or other components of the blood collection device 100.

The venting aperture 142 can be configured to allow venting of the container to atmospheric pressure. In some embodiments, the venting aperture 142 may have a cross-sectional area of between about 0.05 mm$^2$ and about 1.5 mm$^2$, inclusive of all subranges and values therebetween. As described above, it can be desirable to vent to atmospheric pressure at a predetermined rate that does not cause rapid changes in pressure. This can prevent or reduce rapid movement of blood, which can lead to blood cell damage. Therefore, the venting aperture 142 can be configured to vent to atmospheric pressure at average rates of less than about 15 inHg per second, inclusive of subranges or values therebetween, including, for example, about 14 inHg per second. In some embodiments, the rate of venting from vacuum pressure to atmospheric pressure can be less than a maximum rate of about 50 inHg per second, inclusive of subranges and values therebetween. In some embodiments, the venting from vacuum pressure of the blood collection device to atmospheric pressure can be over a predetermined period of time, such as, for example, over at least about 2 seconds of vent time, inclusive of subranges and values therebetween. While the venting aperture 142 is described as being selectively couplable to other components of the blood collection device 100 via a selector valve 140, it can be appreciated that in other embodiments, the venting aperture 142 can be disposed separate from the selector valve 140, e.g., at any suitable location that allows it to vent air into the container 110. In such cases, a user can manually open and/or close the venting aperture 142 when needed for venting, or the venting aperture 142 can be designed to be sufficiently small to remain open for continual, slow venting of pressure in the container 110. In embodiments described herein, the venting aperture 142 can be disposed relative to the container 110 (or coupled to the container 110) at a location that is not in line with fluid flow (e.g., blood, clot, etc.) into the container 110. This can avoid or reduce the mixing of air with the blood flow, which can lead to undesirable bubbles or blood foam within the blood.

In some embodiments, the blood collection device 100 may be configured to draw fluid into a reservoir of a container 110 using negative pressure and drive fluid out of the reservoir using positive pressure. For example, a port may be coupled to the container 100 and configured to receive air into the container 110 to generate a positive pressure within the reservoir to drive the volume of fluid (e.g., blood) through the filter 112 such that a plurality of particulates (e.g. clot material) are filtered from the volume of fluid and to output at least a portion of the volume of fluid into the extraction device (e.g., second vacuum source) when the extraction device is coupled to the output (e.g., outlet 120). In some embodiments, the port used to drive the fluid using positive pressure may be the same port used to draw fluid into the reservoir using negative pressure (e.g., the vacuum port coupled to the vacuum conduit 162). For example, the vacuum conduit may be couplable to the reservoir via the port and may be configured to deliver the air into the container 110 via the port to generate the positive pressure. Alternatively, the extraction device may generate negative pressure within its volume while the reservoir is at atmospheric pressure to draw fluid from the reservoir into the extraction device.

Blood Collection Device

Figure 2A:
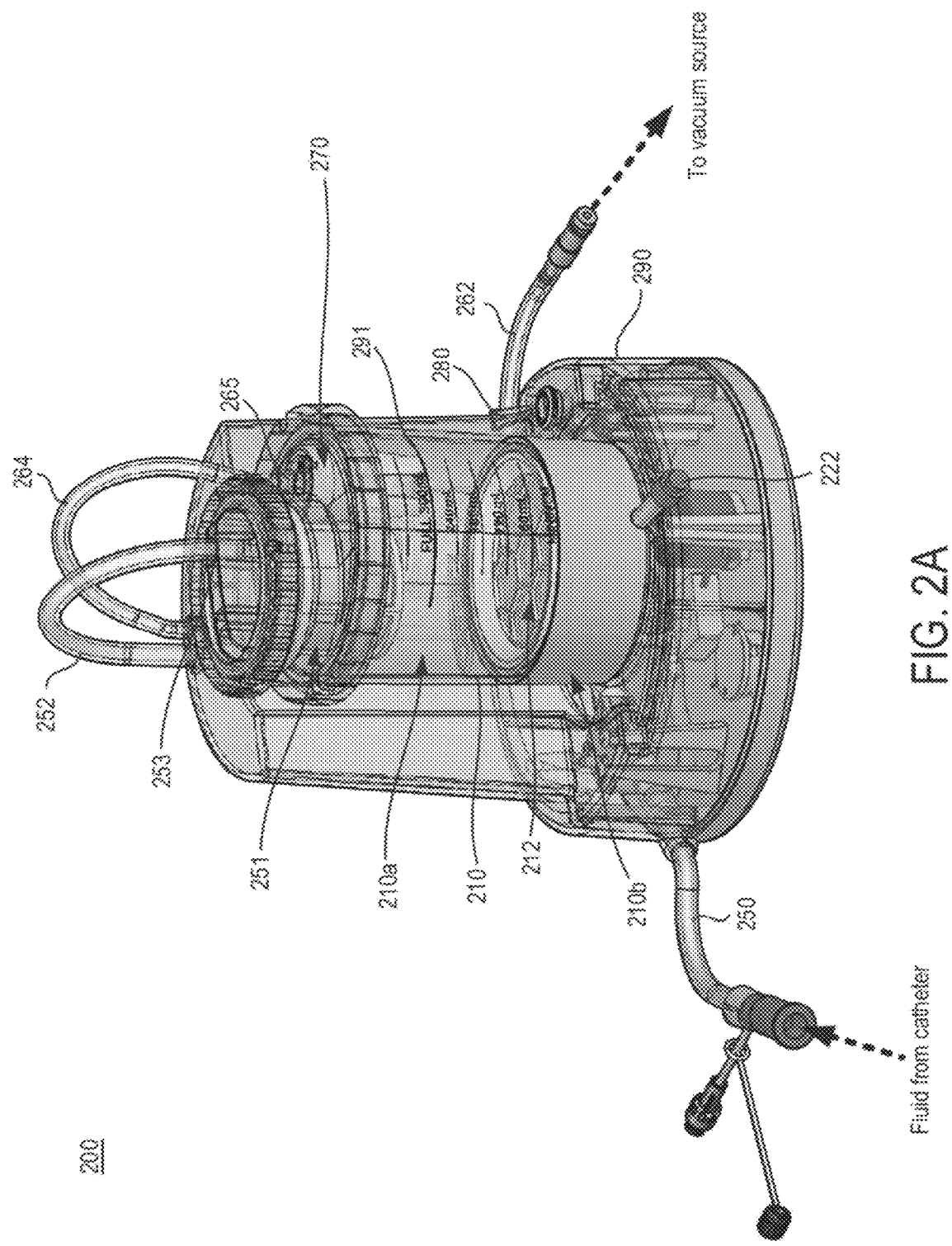
FIGS. 2A, 2B, and 2D are schematic perspective views of a blood collection device, according to embodiments.
Figure 2B:
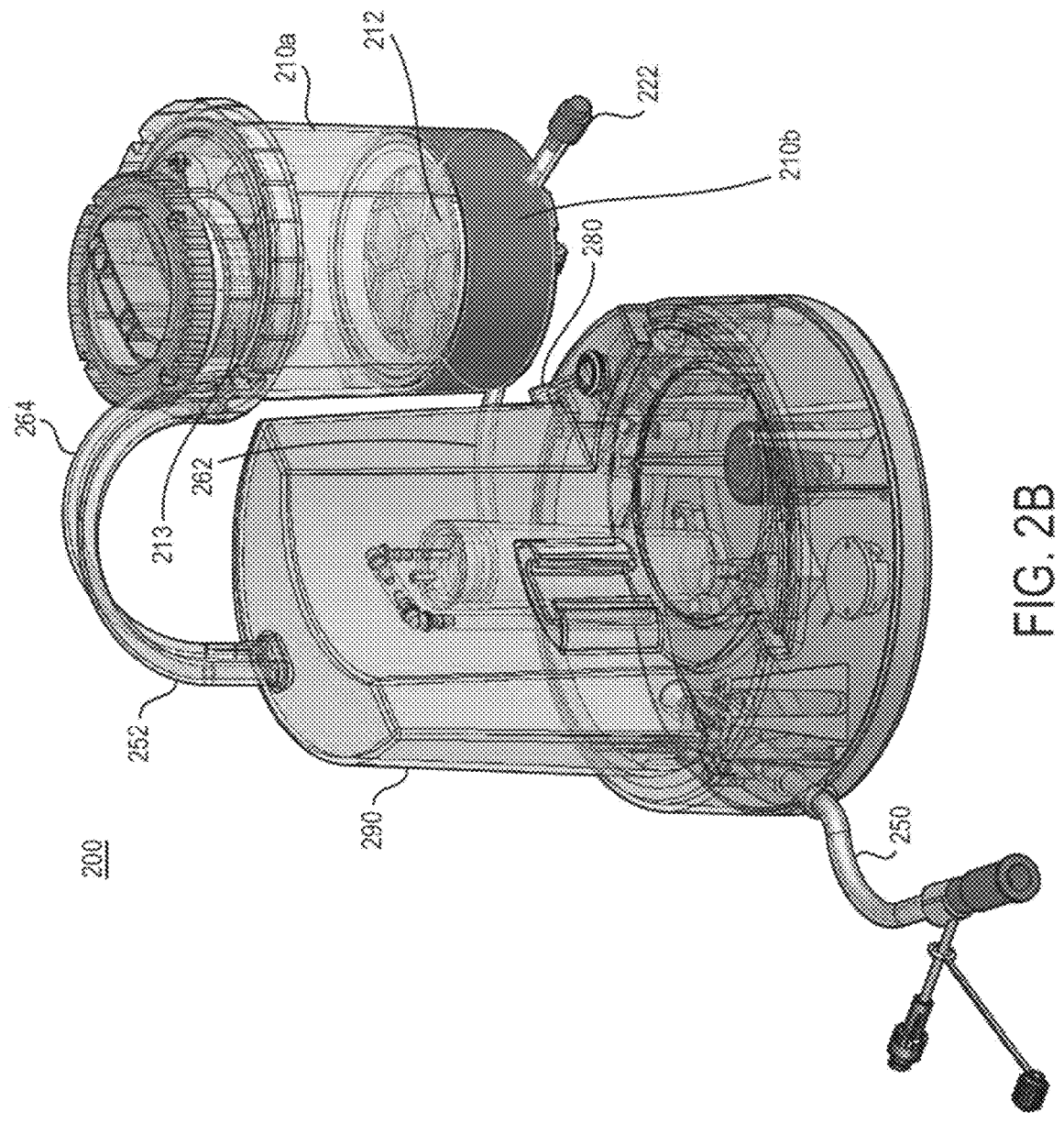
Figure 2C:
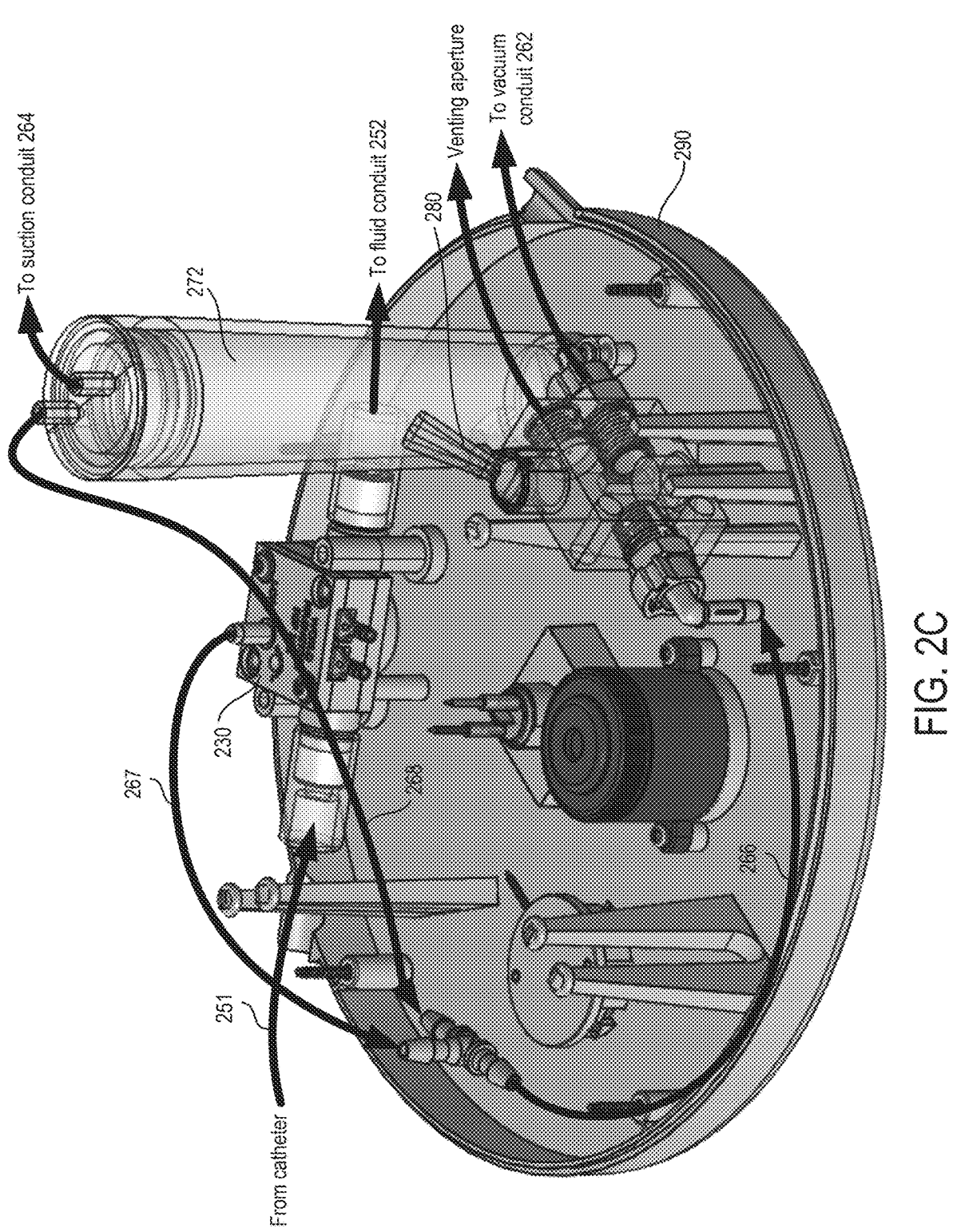
FIG. 2C is a diagram showing internal connections of the blood collection device shown in FIGS. 2A and 2B.
Figure 2D:
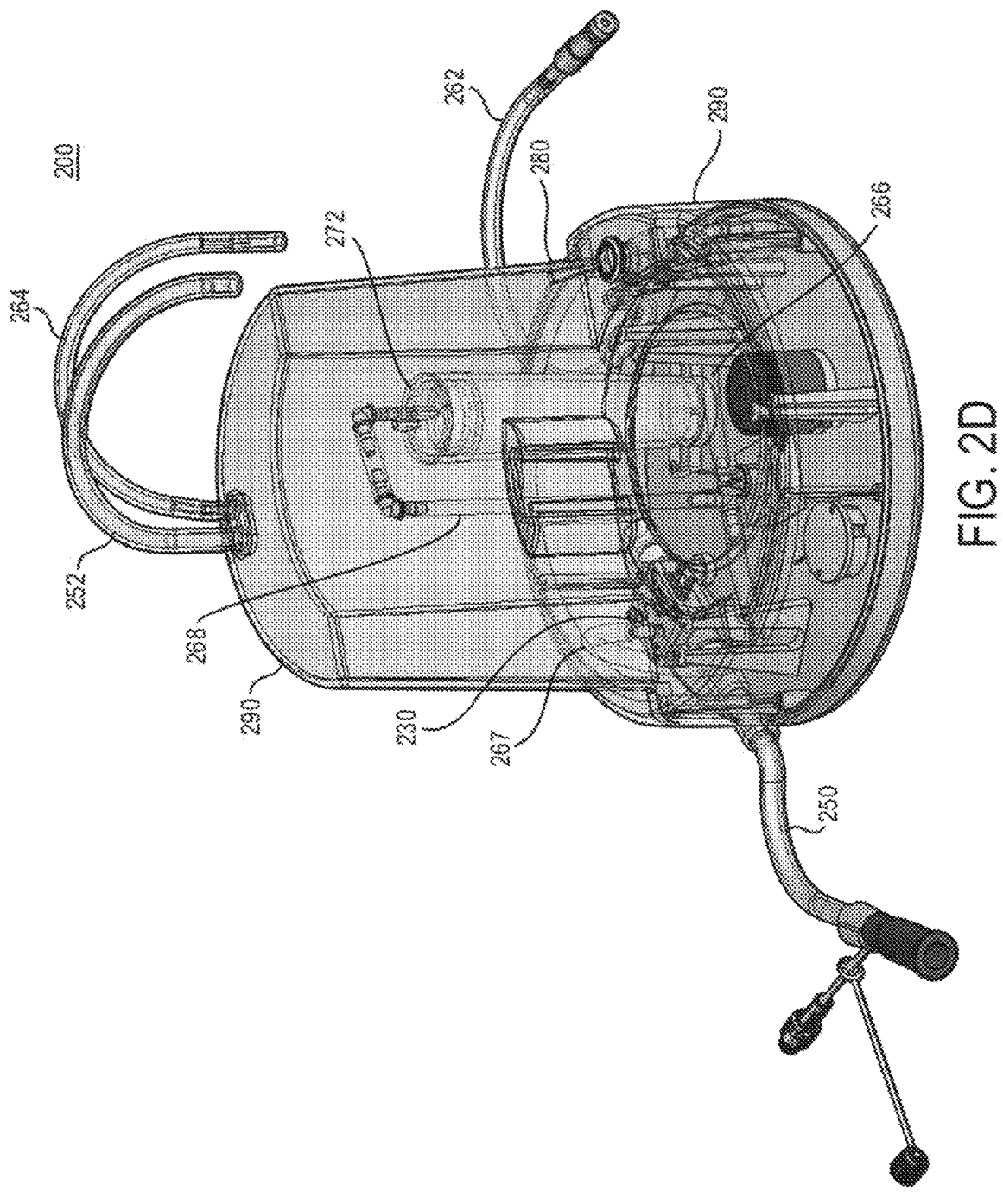
Figure 2E:
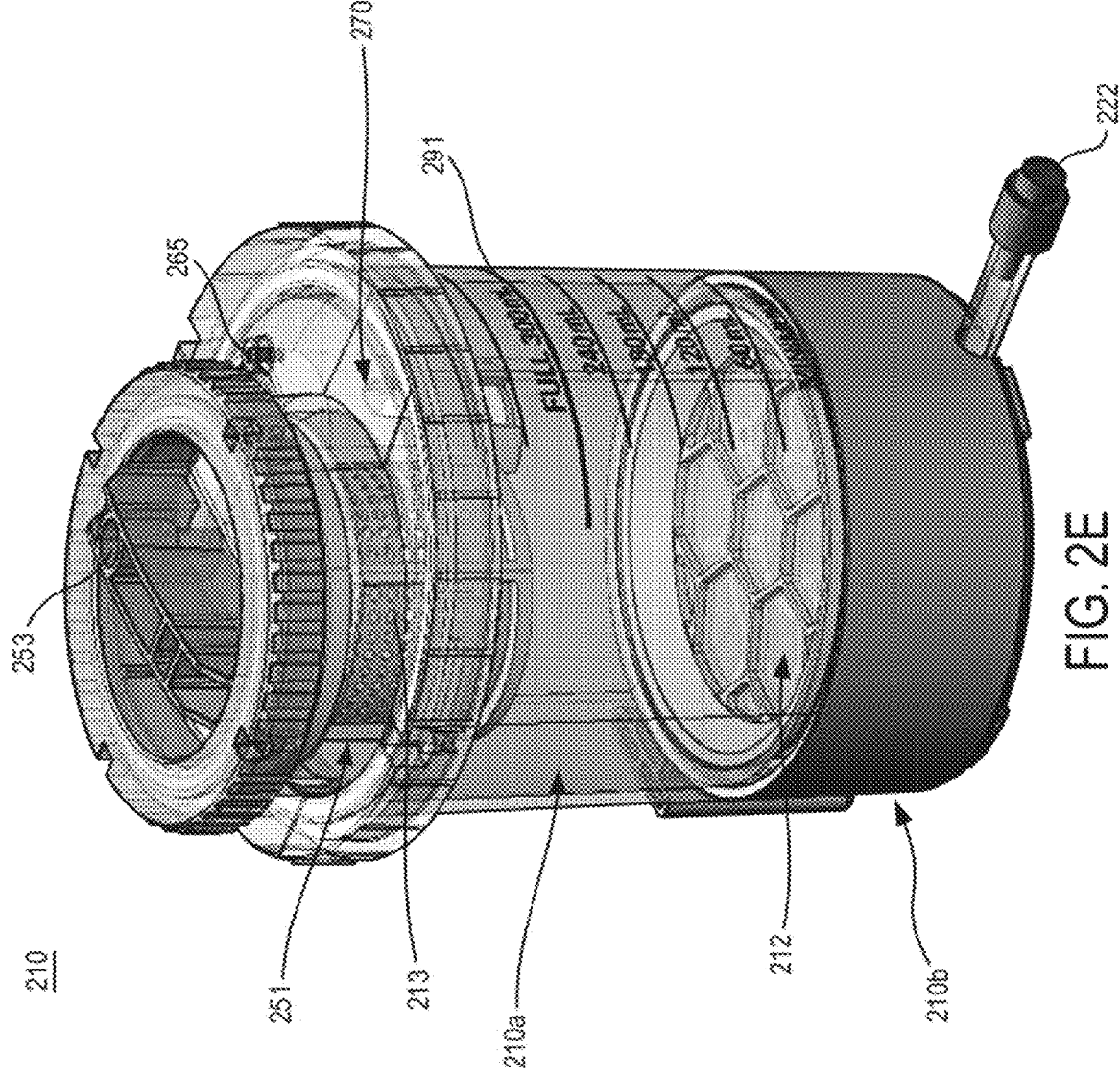
FIG. 2E is a schematic perspective view of a container of the blood collection device shown in FIGS. 2A and 2B.

FIGS. 2A, 2B, and 2D show perspective views of a blood collection device 200, which can be structurally and/or functionally similar to other blood collection devices described herein, including the blood collection device 100 of FIG. 1. FIG. 2C depicts inner components of the blood collection device 200, where connections and fluid paths between various components are shown. FIG. 2E shows a perspective view of a container 210 of the blood collection device 200.

The blood collection device 200 may comprise a container 210, a filter 212 disposed in the container 210, fluid conduits 250, 252, vacuum conduits 262, 264, a switch 280, and a housing 290. As shown in FIG. 2C, the blood collection device 200 may further comprise a flow sensor 230. In some embodiments, the fluid conduit 250, 252 may be coupled to a catheter assembly (e.g., such as catheter assembly 10 or any suitable aspiration device), which can be disposed in the patient and be configured to remove clot from a patient. The fluid conduit 250, 252 may be coupled between the aspiration catheter and the container 210. The fluid conduit 250, 252 can be in fluid communication with a vacuum source (e.g., such as vacuum source 160), via a fluid path that extends through the container 210. In some embodiments, the fluid conduit 250, 252 may have a cross-sectional area that remains the same or increases in a direction of flow toward the container 210, e.g., to avoid a decrease in pressure below a vapor pressure of the blood. In some embodiments, the fluid conduit 250, 252 may have an inner diameter of between about 0.15 inches and about 0.3 inches, inclusive of all subranges and values therebetween. The vacuum source may be configured to apply negative suction to draw fluid such as blood, saline, and/or clot from the catheter assembly into the container 210.

The fluid conduit 250 may be coupled to an inlet or inlet port 253 of a flow sensor 230. As shown in FIG. 2C, a flow path 251 defined by the fluid conduit 250 can be coupled to the flow sensor 230. The flow sensor 230 may further be coupled to the vacuum conduit 262 that is coupled to the vacuum source, via flow paths 266, 267. The vacuum conduit 262 can be coupled to the switch 280. In some embodiments, the switch 280 can be configured to couple the suction conduit 262 to one or more components of the blood collection device 200. For example, when the switch 280 is turned off (e.g., in a first configuration), it can shut off vacuum pressure to the blood collection device 200 and catheter assembly. When the switch 280 is turned on (e.g. in a second configuration), it can deliver vacuum pressure to the blood collection device 200 and catheter assembly. Alternatively or additionally, in some embodiments, the switch 280 can be actuated to selectively couple the vacuum conduit 262 or a venting aperture to the path 266 and other components of the blood collection device 200. For example, the switch 280 can be configured to transition a selector valve (e.g., selector valve 140) between two configurations, e.g., a first configuration in which the selector valve couples the vacuum conduit 262 to the path 266, the container 210 (which in turn is coupled to the catheter assembly and therefore delivers vacuum pressure to the catheter assembly), and/or other components of the blood collection device 200, and a second configuration in which the selector valve couples a venting aperture to the path 266, the container 210, and/or other components of the blood collection device 200. As described above with reference to FIG. 1, the venting aperture can be configured to bring the pressure within the container 210 closer to atmosphere, e.g., for facilitating removal of blood from the container 210.

The flow sensor 230 may be configured to detect differences in the pressure in the fluid conduit 250 compared to the pressure in the vacuum conduit 262, e.g., for monitoring a flow rate of the fluid in the fluid conduit 250. The flow sensor 230 can be structurally and/or functionally similar to the flow sensor 130. In some embodiments, the flow sensor 230 can be implemented as a pressure differential switch, which can include a membrane that displaces depending on the pressure in the fluid conduit 250 relative to the vacuum reference (e.g., pressure in the vacuum conduit 262). In some embodiments, an output device (e.g., audio device, display, lighting, etc.) may be coupled to the flow sensor 230 and be configured to output a notification or alert to the user based on the flow rate in the fluid conduit 250, e.g., as monitored using the flow sensor 230. For example, a determined flow rate above a predetermined threshold (e.g., or an increase in pressure in the fluid conduit 250 relative to the vacuum conduit 262) may trigger the output device to output a notification or alert (e.g., user-perceptible signal, audible alert, warning, beep, or visual light). The alert can indicate to a user (e.g., medical professional) that the catheter assembly coupled to the fluid conduit 250 is withdrawing blood without clot. The user can then stop the application of vacuum, e.g., by releasing an actuator (e.g., button) or other component controlling the application of vacuum pressure to the catheter assembly. For example, as described above, the user can release an actuator on a handle of a catheter assembly to shut off or close a valve, which then decouples (e.g., isolates) the vacuum pressure from the blood collection device 200 to the catheter of the catheter assembly.

The container 210 (e.g., reservoir, canister) may be configured to receive a volume of fluid (e.g., blood, clot, thrombus, and/or other fluids) from the fluid conduit 250 via a fluid conduit 252. In some embodiments, the container 310 can include a marking 291 (e.g., "FULL 300 mL" line) indicating a maximum fluid fill line. The fluid conduit 252 may be coupled between an outlet of the flow sensor 230 and an inlet of the container 210. The inlet may be configured to receive the fluid and be disposed near a first end of the container 210. The fluid conduit 252 may therefore be configured to transport fluid from the fluid conduit 250 to the container 210. In some embodiments, the fluid conduit 252 can be configured to have a predetermined length. The length of the fluid conduit 252 can be configured to sufficiently displace or separate the fluid conduit 250 from the source of vacuum pressure (e.g., conduit 262 coupled to vacuum source), such the measured pressure of the fluid conduit 250 corresponds more closely to (e.g., more accurately reflects) the pressure within the catheter assembly. In some embodiments, the length of the fluid conduit can be between 2 feet and 10 feet, inclusive of all subranges and values therebetween.

A vacuum conduit 264 may couple the vacuum source (e.g., continuous vacuum source, vacuum pump, etc.) to the container 230. The vacuum conduit 264 can be coupled to the container 230 at a port or vacuum port 265. The vacuum conduit 264 can be coupled to a vacuum conduit 262, via flow paths 266 and 268 (as depicted in FIG. 2C). The vacuum conduit 262 can be couplable to a the vacuum source. The vacuum conduit 264, when coupled to the vacuum source, can then generate negative pressure within the container 210, which in turn is coupled to the fluid conduit 250 and the catheter assembly, so that vacuum pressure can be applied to the catheter assembly to engage, ingest, and withdraw a clot and blood into the container 210.

As shown in FIG. 2E, the container 210 can be divided into two separate chambers or regions 210a, 210b, by a filter 212. The filter 212 can be structurally and/or functionally similar to the filter 112. For example, the filter 212 can be configured to filter blood that passes from the first chamber 210a through the filter 212 to the second chamber 210b. The filter can be configured to remove particulates (e.g., clot, thrombus) from the blood. In some embodiments, fluid that has been filtered by the filter 212 can be removed from the container 210. For example, an outlet 222 can be coupled to the container 210 at a location along the second chamber 210b, allowing a user to withdraw filtered fluids from the chamber 210b. The user can couple an extraction device, a vacuum source, or other blood or fluid collection device (e.g., a syringe, a pre-vacuumed sample collection container) to the outlet 222 to draw out filtered fluids. The extraction device or vacuum source can be configured to generate negative pressure to draw at least a portion of the volume of fluid within the container through the filter 212 and into the extraction device or vacuum source. While fluid is being drawn out of the container 210, additional fluid (including blood) in the chamber 210a can flow through the filter 212 and into chamber 210b, e.g., via gravity and/or the vacuum being applied by the syringe or collection device.

In some embodiments, the container 210 can include a coarse filter or a grating 213 (e.g., a first filter). The grating 213 can be configured to remove a first portion of particulates (e.g., clot, thrombus) within the volume of fluid which are larger in size than those removed by the filter 212. Blood delivered to the container 210 can first pass through the grating 213, which can remove the larger size particulates. Then, when the container 210 is coupled to an extraction device (e.g., a syringe) via outlet 222, the extraction device can be configured to generate suction or negative pressure to draw the blood through the filter 212. The filter 212 can then remove a second portion of particulates that are smaller in size. The grating 213 may be disposed within the container 210 upstream of the filter 212.

In some embodiments, the grating 213 can be supported on or form part of an inlet assembly 251, which can include the inlet that is couplable to the fluid conduit 252 and a catch container (e.g., a container, can, tray, etc.). The catch container can include the grating 213. In some embodiments, the inlet assembly can be removed from or decoupled from the container 210. As such, a physician may remove the inlet assembly during a procedure to visually examine whether larger clot or thrombus has been effectively ingested by the aspiration catheter and captured in the blood collection device 200. The inlet assembly can be coupled to the container 210 via a screw fit, friction fit, or other mechanical fit.

In embodiments where the container 210 includes a grating 213 and a filter 212, the grating 213 can be referred to as a first filter or coarse filter, and the filter 212 can be referred to as a second filter or fine filter. The first filter may be disposed within the container downstream from the inlet of the container. The first filter may include openings having a first size and being configured to filter particulates having a size greater than the first size. The second filter may be disposed within the reservoir downstream from the first filter and upstream of the outlet of the container. The second filter may be separate from the first filter and disposed near the second end of the container. The second filter may include openings having a second size and being configured to filter particulates having a size greater than the second size where the second size is smaller than the first size.

In some embodiments, the fluid conduits 250, 252, interfaces between the fluid conduits 250, 252, and chamber or region 210b of the container 210 may be filled with fluid (e.g., a priming fluid such as, for example, saline), e.g., prior to applying vacuum pressure to draw or pull blood and/or clot into the container 210. The fluid in the fluid conduits 250, 252, interfaces between the fluid conduits 250, 252, and chamber 210b of the container 210 can minimize or reduce mixing or introduction of air into the blood. In some embodiments, interfaces between the catheter assembly, the fluid conduits 250, 252, and the container 210 can be vacuum sealed to prevent external (e.g., atmospheric) air from unintentionally mixing with the blood, thereby reducing foaming.

In embodiments, the vacuum conduit 264 can be coupled to the container 210 at a float valve 270. The float valve 270 can prevent or reduce the travel or blood or other fluids into the vacuum conduit 264, e.g., to prevent or reduce the risk of fluid travelling into the vacuum path(s) and disrupting the operation of the vacuum source. For example, the ball valve 270 may be disposed at a vacuum port or location where the vacuum conduit 264 is coupled to the container. During operation of the blood collection device to capture fluid and/or clot, the valve can remain open, e.g., to allow negative pressure to be generated within the reservoir to draw the fluid into the reservoir. However, if the fluid within the container reaches a predetermined level (e.g., a maximum fill line 291 or higher), then the valve can be configured to close to block the vacuum port, e.g., to prevent overflow of the fluid from the reservoir into a vacuum conduit coupled to the vacuum port. In some embodiments, an additional tube, container, or canister 272 can be coupled in line with the vacuum conduit 264 (or the vacuum path from the container to the vacuum source) to further prevent or reduce the travel or blood or other fluids into the vacuum path(s) and disrupting the operation of the vacuum source. For example, the vacuum port may be coupled to the vacuum source via a vacuum path that passes through an overflow tube such that the overflow tube can capture any fluid that overflows into the vacuum path.

Flow Sensor

In some embodiments, a flow sensor of a blood collection device may be configured to measure or monitor a flow rate of fluid within the fluid conduit being received from a patient, e.g., via a catheter assembly or aspiration catheter (e.g., catheter assembly 10). In some embodiments, the flow sensor can be coupled to an output device, controller, or other components, which can operate to notify a user of the state of clot removal of the catheter assembly or aspiration catheter. For example, an output device can be configured to output one or more signals (e.g., audio, visual, etc.) to a user, to indicate to the user whether the catheter assembly or aspiration catheter has engaged with a clot, is ingesting a clot, and/or is proximally transporting a clot toward a container (e.g., container 110, 210). By knowing the state of clot removal, a user can then determine whether to continue applying vacuum pressure and/or to reduce or terminate the application of vacuum pressure, e.g., to avoid unnecessary blood loss.

In some embodiments, the flow sensor may be a differential pressure switch that is configured to compare the pressure in a fluid conduit coupled to the catheter assembly to the pressure in a vacuum reference (e.g., a vacuum conduit). A relatively low pressure difference between the reference suction pressure and the fluid conduit pressure may indicate a relatively low flow rate, which can correspond to clot digestion/withdrawal and low blood loss. By contrast, a relatively high pressure difference between the fluid conduit pressure and the reference vacuum pressure (e.g., a difference greater than a predetermined threshold) may indicate a relatively high flow rate, which can correspond to high blood loss with relatively low clot removal. Continued application of suction or vacuum pressure with a high flow rate can unnecessarily remove blood from the patient. Furthermore, due to the length of the catheter assembly (e.g., as needed to reach the necessary target site in a patient's vasculature) and the length of the fluid conduit to the blood collection device, a significant volume of blood may be withdrawn from the patient before a user (e.g., medical professional) may be able to visually confirm in the blood collection device that a clot has already been removed. Accordingly, in some embodiments, an output device may be coupled to the flow sensor and configured to generate a notification or alert to the user when the determined flow rate is above a predetermined threshold, thereby enabling the user to release suction and reduce blood loss.

Figure 3:
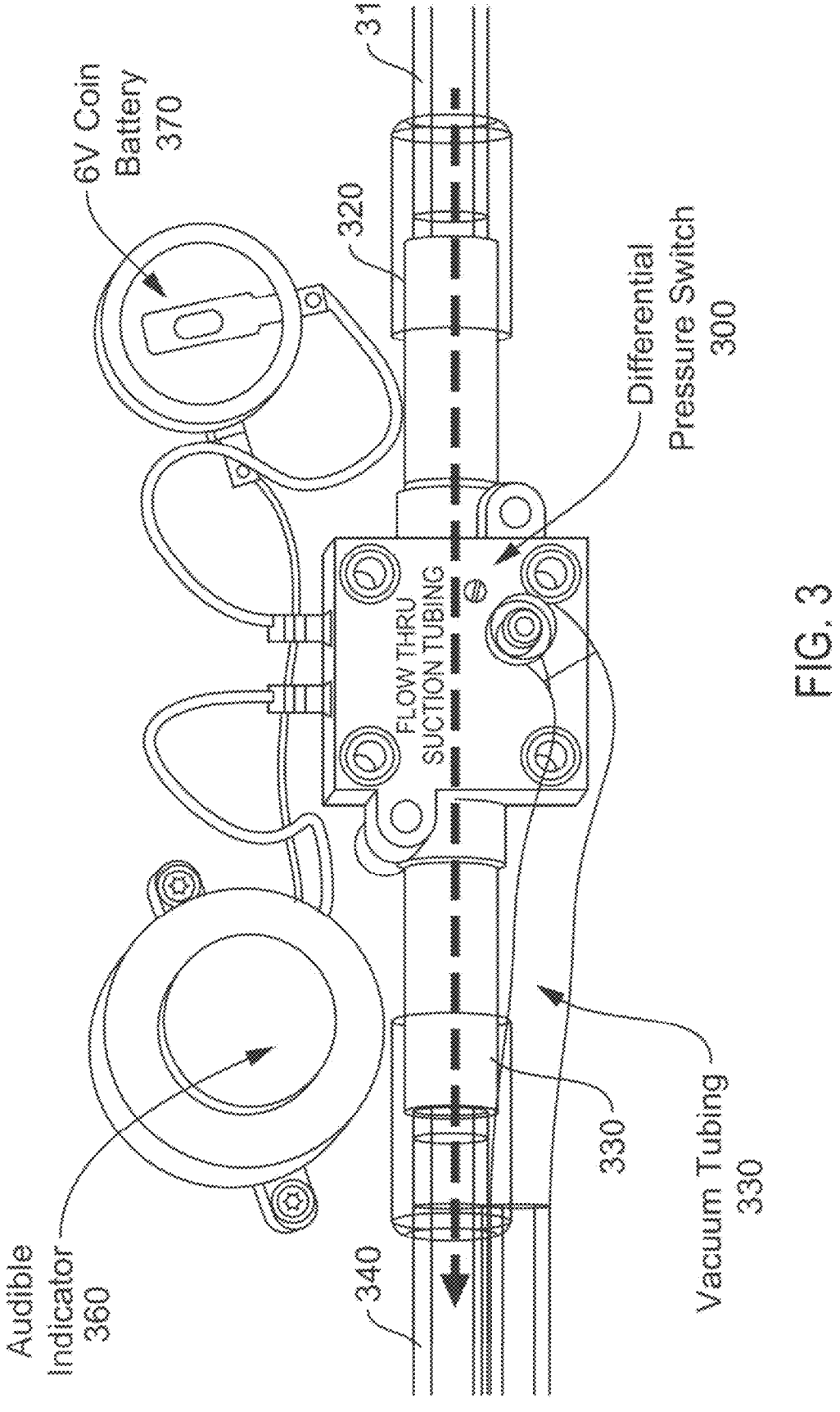
FIG. 3 is a schematic diagram of a flow sensor of a blood collection device, according to embodiments.

FIG. 3 is a schematic diagram of a flow sensor 300 of a blood collection device such as, for example, blood collection devices 130, 230. The flow sensor 300 may be implemented as a differential pressure switch 300 coupled to an output device 360 and a power source 370. An inlet 310 of the sensor 300 may be coupled to a fluid conduit 310 such as, for example, fluid conduit 150, 250. The fluid conduit 310 can be fluidically coupled to a catheter assembly (e.g., catheter assembly 10) or aspiration catheter. An outlet 330 of the sensor 300 may be coupled to a fluid conduit 340 such as, for example, fluid conduit 152, 252. Furthermore, the sensor 300 may be coupled to a vacuum conduit 330 such as, for example, suction conduit 162, 262. The suction conduit 330 may function as a reference pressure line for the differential pressure switch 350 to compare against the pressure of the fluid flowing through the sensor 300 from the fluid conduit 310. A differential pressure switch advantageously provides an in-line design that prevents or reduces the risk that the flow sensor 300 would clog with one or more clot pieces. In contrast, flow sensors such as T-sensors having a side line may be more prone to clogging that can reduce the accuracy of the sensor reading.

In some embodiments, an output device 360 (e.g., audio device, display, light indicator, etc.) may be coupled to the differential pressure switch 350 and configured to output a notification or alert to the user based on the determined flow rate of the fluid conduit 310. For example, a determined flow rate above a predetermined threshold may trigger the output device 360 to output a notification (e.g., audible alert, warning, beep) that the suction applied is substantially withdrawing blood without clot from the patient. In some embodiments, the notification may be provided for one or more of a plurality of states including a first flow rate (e.g., substantially no flow), a second flow rate (e.g., moderate flow), and a third flow rate (e.g., high flow). Each of these flow rates can correspond to a different stage of clot removal from a patient. For example, clot engagement and/or initial ingestion may correspond to the first flow rate where flow through the first conduit 310 is relatively low as clot pieces are macerated and aspirated. Low flow rate may correspond to active clot digestion, e.g., suggesting that continued application of suction is desired. High flow rate can correspond to blood being drawn into the fluid conduit 310 without clot, e.g., suggesting to the user that vacuum pressure application should be reduced or terminated to reduce blood loss. In some embodiments, systems and devices described herein can include a controller (e.g., processor), which can be configured to automatically control the vacuum pressure application based on the determined flow rate. For example, application of vacuum pressure may be automatically stopped when a flow rate above a predetermined flow rate (e.g., third flow rate) is determined.

As described above, the fluid conduit 340 can be configured to carry the fluid from the fluid conduit 310 to a container (e.g., container 110, 210). In some embodiments, the fluid conduit 340 may comprise a predetermined length to enable sufficient accuracy in measuring the pressure of the fluid conduit 310 by the flow sensor 300. For example, the fluid conduit 340 may comprise a length of about 4 feet to about 8 feet, about 5 feet to about 7 feet, about 4 feet, about 5 feet, about 6 feet, about 7 feet, and about 8 feet, including all ranges and sub-values in-between.

Container

Generally, a container of a blood collection device may be configured to receive, filter, and/or store blood, e.g., for blood sampling, for autologous transfusion, for reinfusion, etc. The container may be configured to provide a number of benefits including: filtration to remove particulates; controlled venting of the blood to atmospheric pressure to reduce hemolysis and prepare the blood for transfusion; atraumatic container geometry to reduce blood foaming and hemolysis; integration with a flow sensor in a compact form factor that may be utilized within a sterile field; and/or elimination of a non-sterile suction pump waste cannister.

Figure 4A:
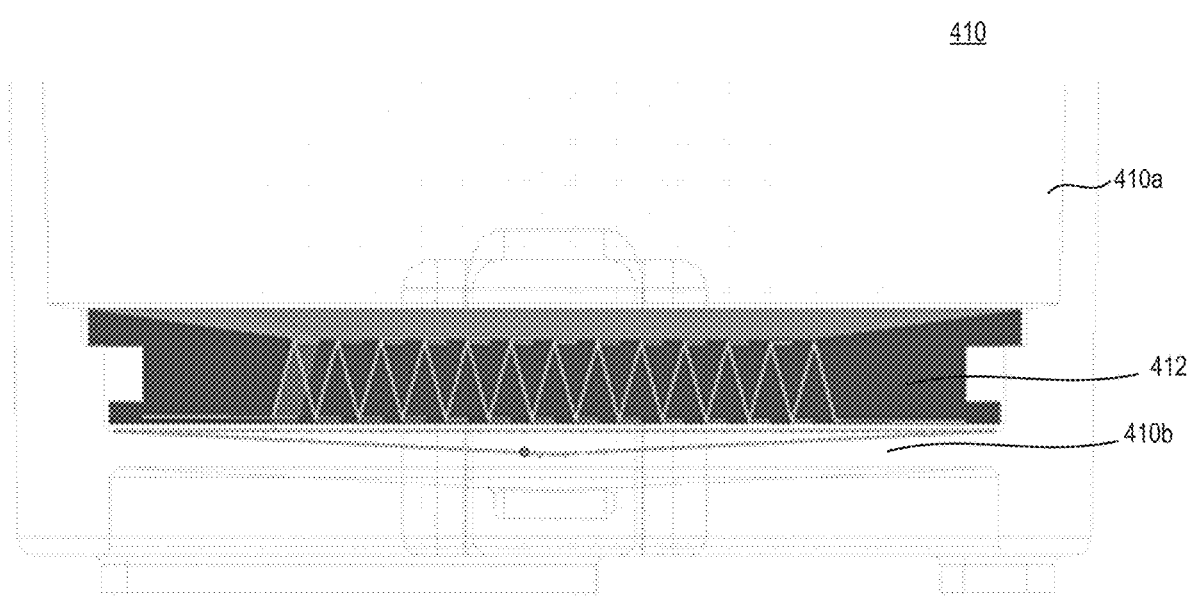
FIG. 4A is an image of a blood collection device, according to embodiments.

In embodiments described herein, a container of a blood collection device can include one or more regions or volumes that are separated by a filter. For example, FIG. 4A is a schematic cross-sectional diagram of a filter 412 coupled in fluid communication between a first region or chamber 410*a* of a container 410 and a second region or chamber 410*b* of the container 410. Fluid (e.g., clot, thrombus, blood) from the patient may be stored and filtered using the container 410. The first chamber 410*a* of the container 410 may be configured to receive the fluid (e.g., blood and thrombus) from a fluid conduit (not shown in FIG. 4A) such as, for example, fluid conduit 152, 252, 340. The first chamber 410*a* may be in fluid communication with the second chamber 410*b* via the filter 412 disposed therebetween. The fluid in the first chamber 410*a* may pass through the filter 412 to remove particulates (e.g., clot, thrombus) such that the filtered blood stored in the second chamber 410*b* is suitable for transfusion (e.g., blood not including air pockets, without blood foam). In some embodiments, the filter 412 may have a flat shape (or substantially flat or disk-like shape) to minimize space for air pockets in the second chamber 410*b*. Alternatively, in some embodiments, the filter 412 may have a conical shape or a pleated shape.

In some embodiments, the filter 412 may be set at an angle relative to horizontal, e.g., in an off-angle configuration where a first portion of the filter is positioned closer to a bottom of the container 410 than a second portion. In some embodiments, the filter 412 may comprise a dual-layer or two-layer filter to remove particulates from the fluid. In some embodiments, the filter 412 may comprise a three-layer filter to remove particulates from the fluid. In some embodiments, the filter 412 may include a single layer or more layers, where one or more layers are set parallel to one another or at angles relative to one another. In some embodiments, each layer of the filter can have openings having diameters between about 15 and about 60 microns, inclusive of subranges and values therebetween, such as for example between about 15 and about 50 microns.

Figure 4B:
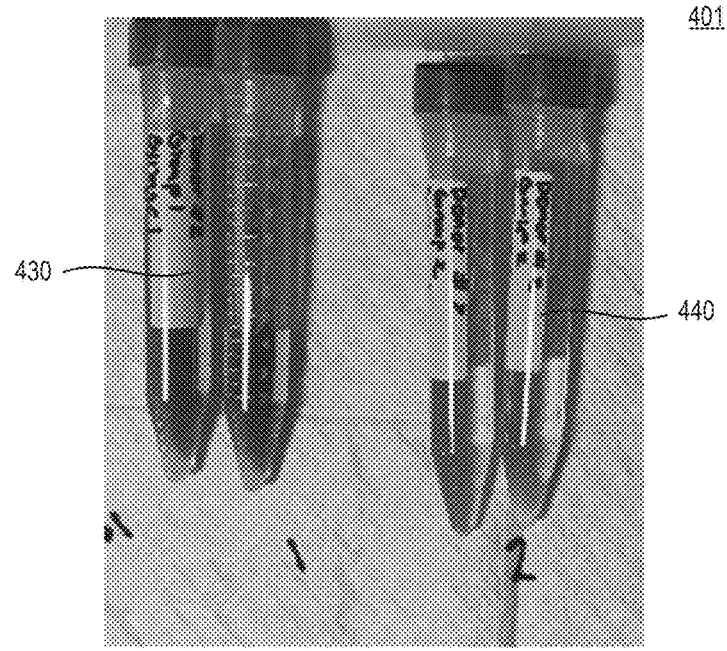
FIG. 4B is an image of a container of a blood collection device, according to embodiments.
Figure 4C:
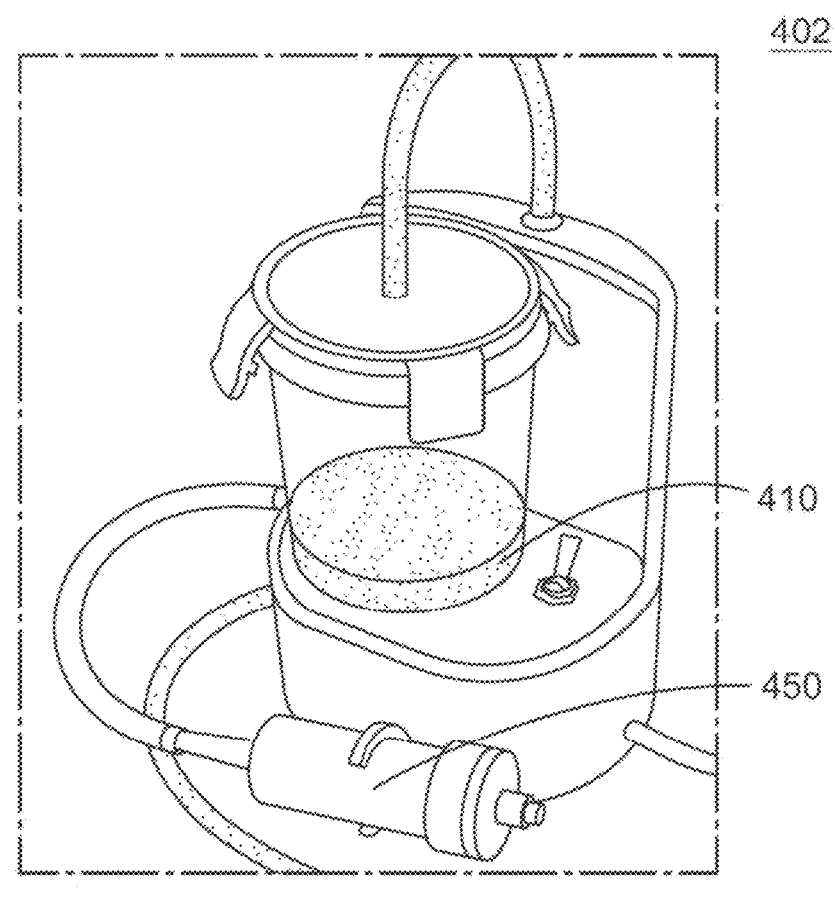
FIG. 4C is a cross-sectional schematic diagram of a container of a blood collection device, according to embodiments.
Figure 4D:
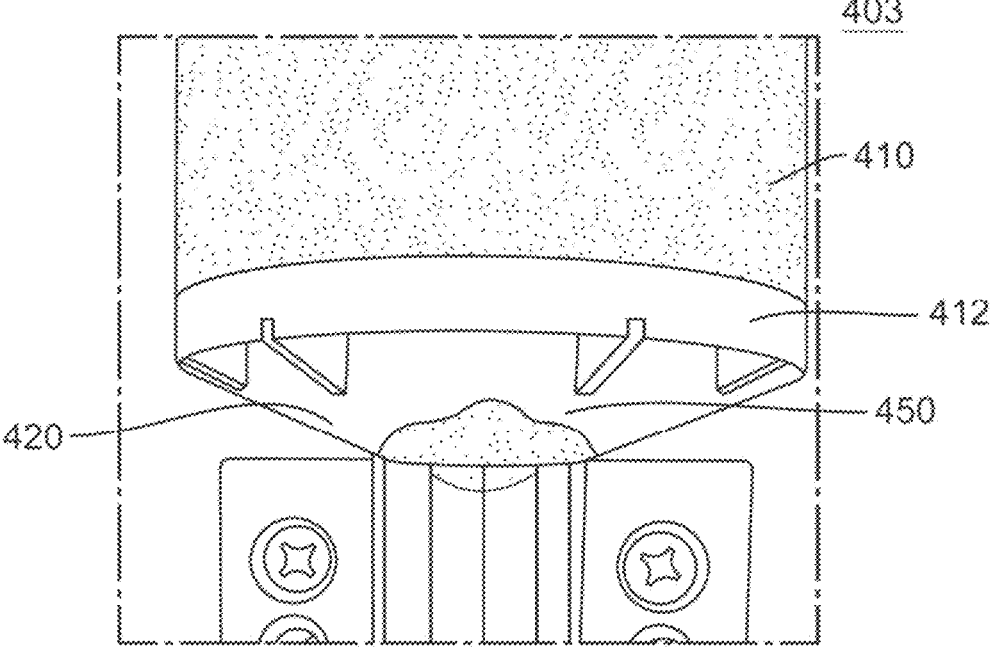
FIG. 4D is an image of blood samples collected by different blood collection devices, according to embodiments.

In some embodiments, due to the size of the openings of the filter mesh, blood may not flow quickly or readily through the filter 412 due solely to gravitational forces, which may lead to an air pocket to form within the second chamber 410*b*. For example, FIGS. 4C and 4D show air pockets 450 that can form beneath the first chamber 410*a* filled with fluid. Blood that enters into a second chamber 410*b* having an air pocket may undergo turbulent mixing leading to hemolysis. As described in more detail in the methods, the blood collection device may be primed to reduce trapped air within the blood collection device. For example, saline can be used to fill the second chamber 410*b* and to submerge (e.g., wet) the filter 412 prior to receiving blood, thereby eliminating air pockets. In other words, a volume of fluid (e.g., saline) may be received in the container to submerge the filter 412 and to fill at least a section of the container disposed downstream of the filter 412 before vacuum is used to draw fluid (e.g., blood, clot) into the container. In some embodiments, air pockets can also be created by design (e.g., where no pressure gradient exists) to drive blood to any empty portion of the device.

While a coarse filter is not depicted in FIG. 4A, it can be appreciated that the container described with reference to FIG. 4A can be structurally and/or functionally similar to other containers described herein. Therefore, the container 410 can include, for example, an outlet port, a coarse filter, an inlet port, a vacuum port, and/or other components as described with respect to other embodiments herein.

In some embodiments, it may be desirable to remove blood from the container. For example, filtered blood may be removed from the container for blood sampling, reinfusion of blood into a patient, or for blood storage and/or collection (e.g., for later transfusion, testing, etc.). Before filtered blood can be removed from the container, the blood received under vacuum must be brought back to atmospheric pressure. However, if the blood received at vacuum pressure in the container 410 is brought to atmospheric pressure too quickly (e.g., at a rate greater than a predetermined threshold), then the blood may undergo rapid and turbulent exchange with air due to the significant pressure gradient, thereby leading to blood foaming, hemolysis, and blood loss. Accordingly, in some embodiments, the fluid stored in the container 410 may be received under vacuum and then pressurized (e.g., brought to atmospheric pressure) within the container 410 at a predetermined rate that reduces hemolysis and facilitate blood transfusion. FIG. 4B is an image 401 of a first blood sample 430 having undergone hemolysis or blood cell damage due to turbulent mixing of blood and air, and a second blood sample 440 collected without having undergone hemolysis or blood cell damage (e.g., using the blood collection devices described herein). In order to reduce hemolysis, one or more vents may be disposed within the container 410 or be couplable to the container 410 via a conduit (e.g., a vacuum conduit), e.g., to facilitate non-turbulent introduction of air into the container 410 through a slow and controlled pressure change. The vents may have a diameter of between about 0.020 inches and about 0.035 inches, including all ranges and sub-values therebetween.

Figure 6B:
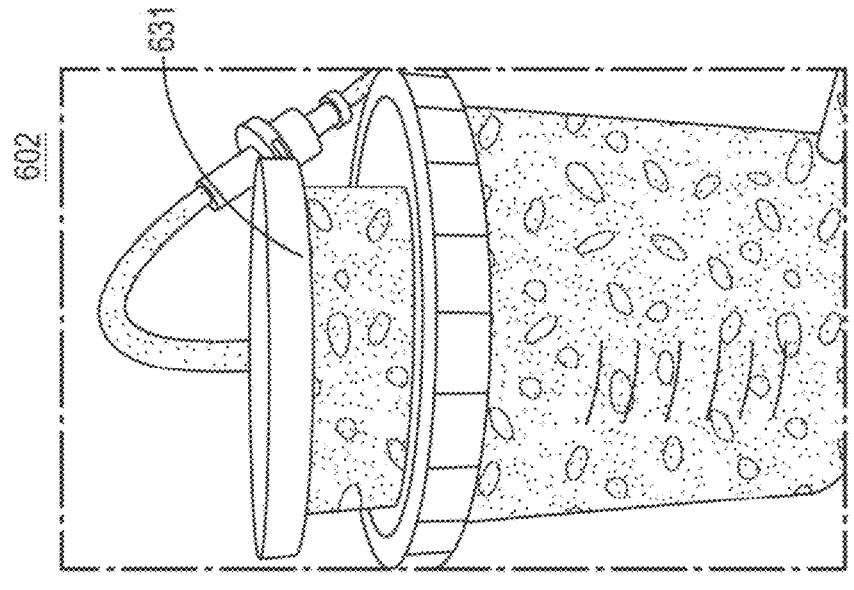
FIG. 6B is an image of a container of a blood collection device, according to embodiments.
Figure 6A:
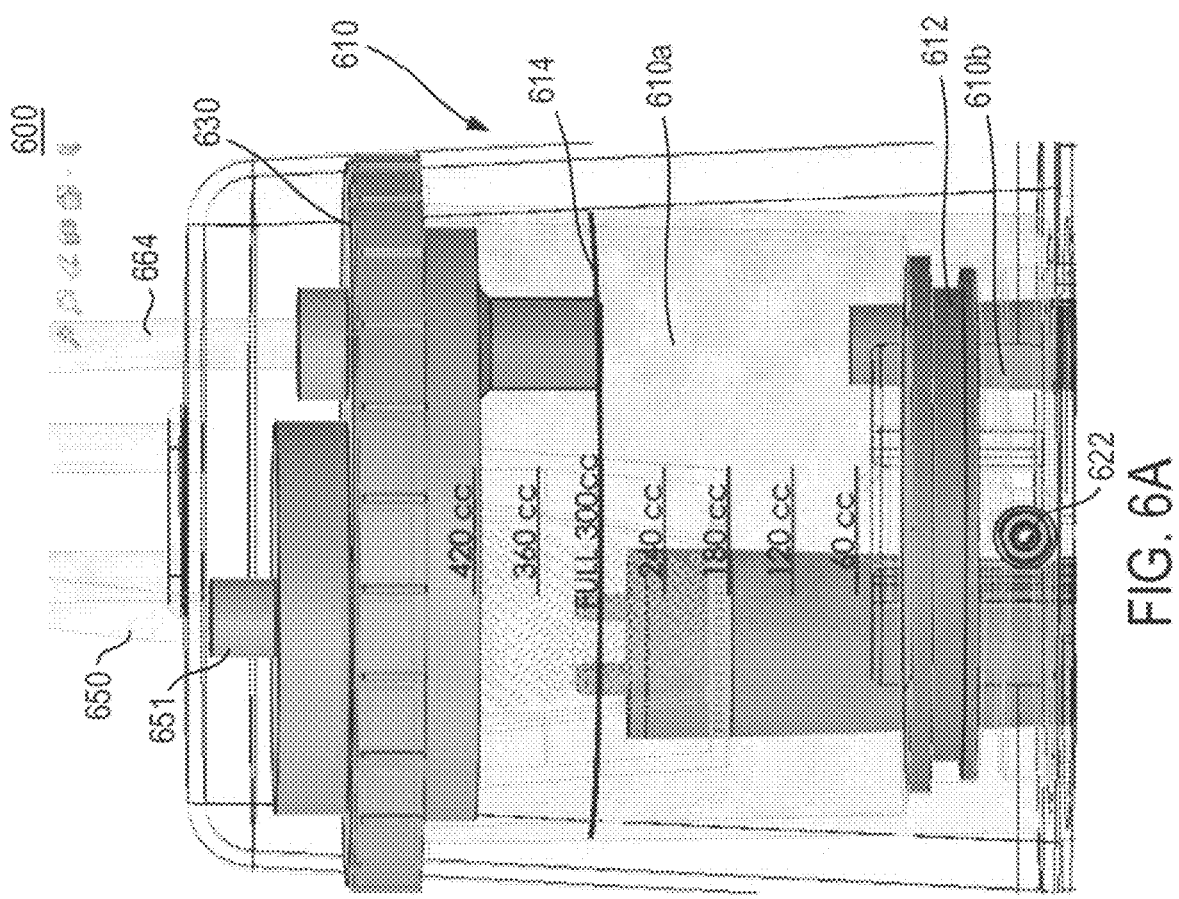
FIG. 6A is a cross-sectional schematic diagram of a container of a blood collection device, according to embodiments.

In some embodiments, the vent may be disposed along the container at a location away from an inlet of a fluid conduit (e.g., away from the fluid flow into the container 410) and adjacent to an outlet of a vacuum conduit, e.g., to reduce turbulent venting. For example, FIG. 6A is a schematic diagram of a blood collection device 600 including a container 610 having a first chamber 610*a* and a second chamber 610*b*, and a filter 612. The blood collection device 600 can be structurally and/or functionally similar to other blood collection devices described herein, including, for example, blood collection devices 100, 200. Fluid may be received into the first chamber 610*a* of container 610 via an inlet port or inlet 651 to which a fluid conduit 650 is coupled. The second chamber 610*b* may comprise or be coupled to an outlet port or outlet 622 for outputting filtered blood. A vacuum conduit 664 may be coupled to the first chamber 610*a* to apply suction to (e.g., generate negative pressure within) the blood collection device 600. A vent 630 may be located adjacent the vacuum conduit 664 and away from the fluid conduit 650 to reduce turbulent flow and hemolysis. By contrast, a vent located near the fluid conduit 650 (e.g., in line with the fluid flow into the container) may contribute to turbulent mixing of air and blood. For example, image 602 in FIG. 6B shows a blood collection device having a vent location 631 corresponding to higher levels of blood foaming due to the vent 631 being in-line with the blood flow.

Alternatively, a vent can be selectively coupled to the container 610, e.g., via a selector valve (e.g., selector valve 140). As described with reference to FIG. 1, a vent (e.g., venting aperture 142) can be selectively coupled to the container 610 by actuating a switch or other actuator of a selector valve, which places the vent in fluid communication with the container. The vent can then deliver air into the container 610 to increase the pressure to atmosphere. The vent can be fluidically couplable to the container via the vacuum conduit 664 or another conduit or port.

As shown in FIG. 6A, the container 610 may include a marking 614 (e.g., "FULL 300 cc" line) indicating a maximum fluid fill line (e.g., similar to maximum fill line 291). To avoid fluid in the container (e.g., blood received in the container) from traveling up through the vacuum conduit 664 to the vacuum source, the vacuum conduit 664 can be coupled to the container 610 at a location above the marking 614 corresponding to the maximum fluid fill line. Moreover, it can be desirable to couple the vent to the container via a conduit or line (e.g., vacuum conduit 664) at a location above the marking 614, e.g., to reduce mixing of air and the volume of fluid (e.g., blood). Furthermore, having the vent be couplable to the container 610 at a location that is spaced apart from the inlet 651 can reduce air bubbling through the blood, thereby reducing the turbulent mixing of air and blood leading to hemolysis.

Figures 5A, 5B:
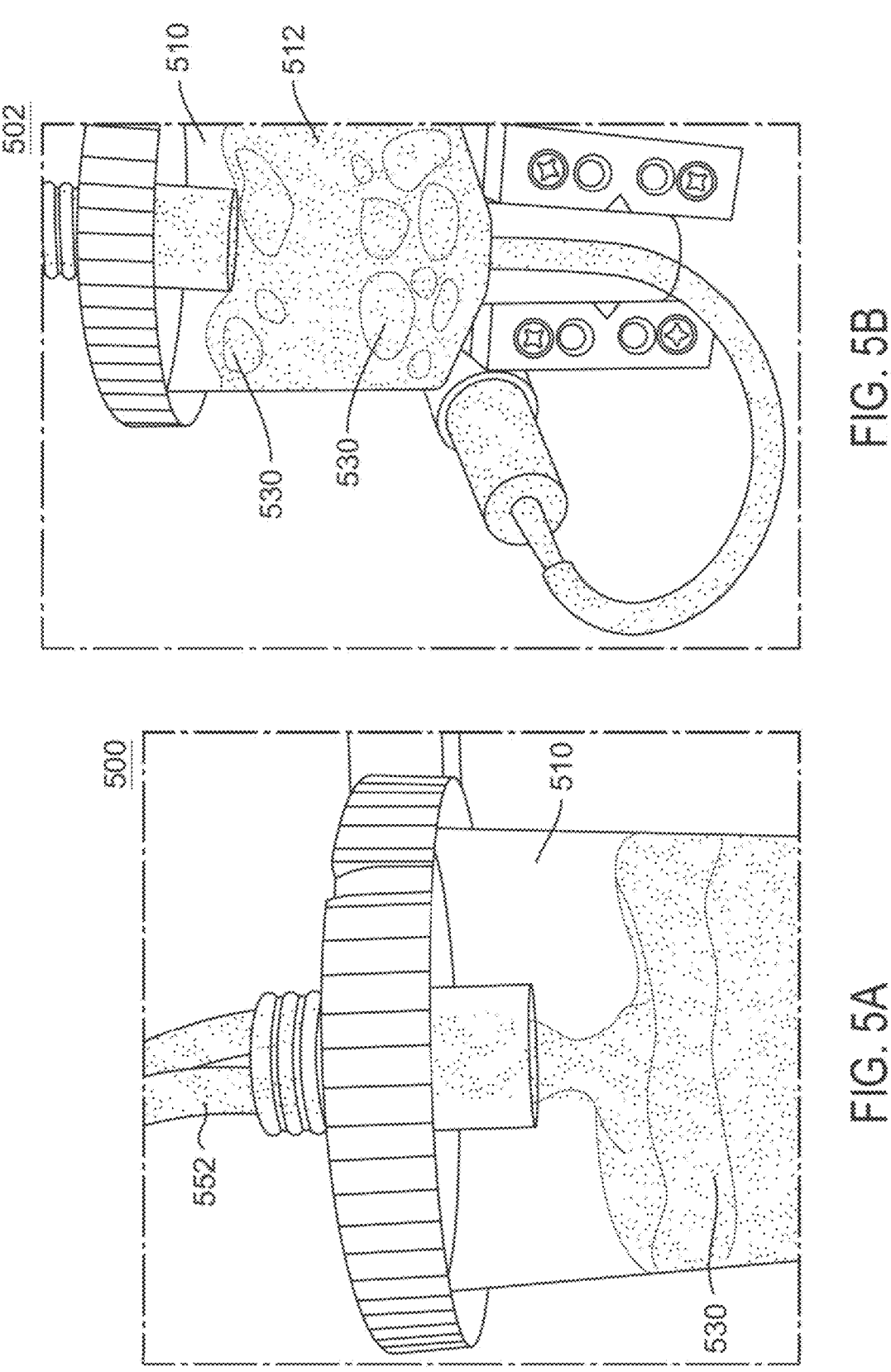
FIGS. 5A and 5B are images of blood foam in a container of a blood collection device, according to embodiments.

Furthermore, in some embodiments, blood foaming may result from improper sealing and air pockets. For example, FIGS. 5A and 5B are images 500, 502 of blood foaming 530 within a container 510 due to an improperly sealed container 510, as shown in the image 500 of FIG. 5A, where a large quantity of blood foaming is formed within the container 510 and inlet fluid conduit 552. Accordingly, each of the interfaces (e.g., connectors) between the fluid conduits to the containers may be vacuum sealed to reduce unintentional mixing of atmospheric air with the blood and thereby reduce foaming and blood loss.

Figures 7A, 7B:
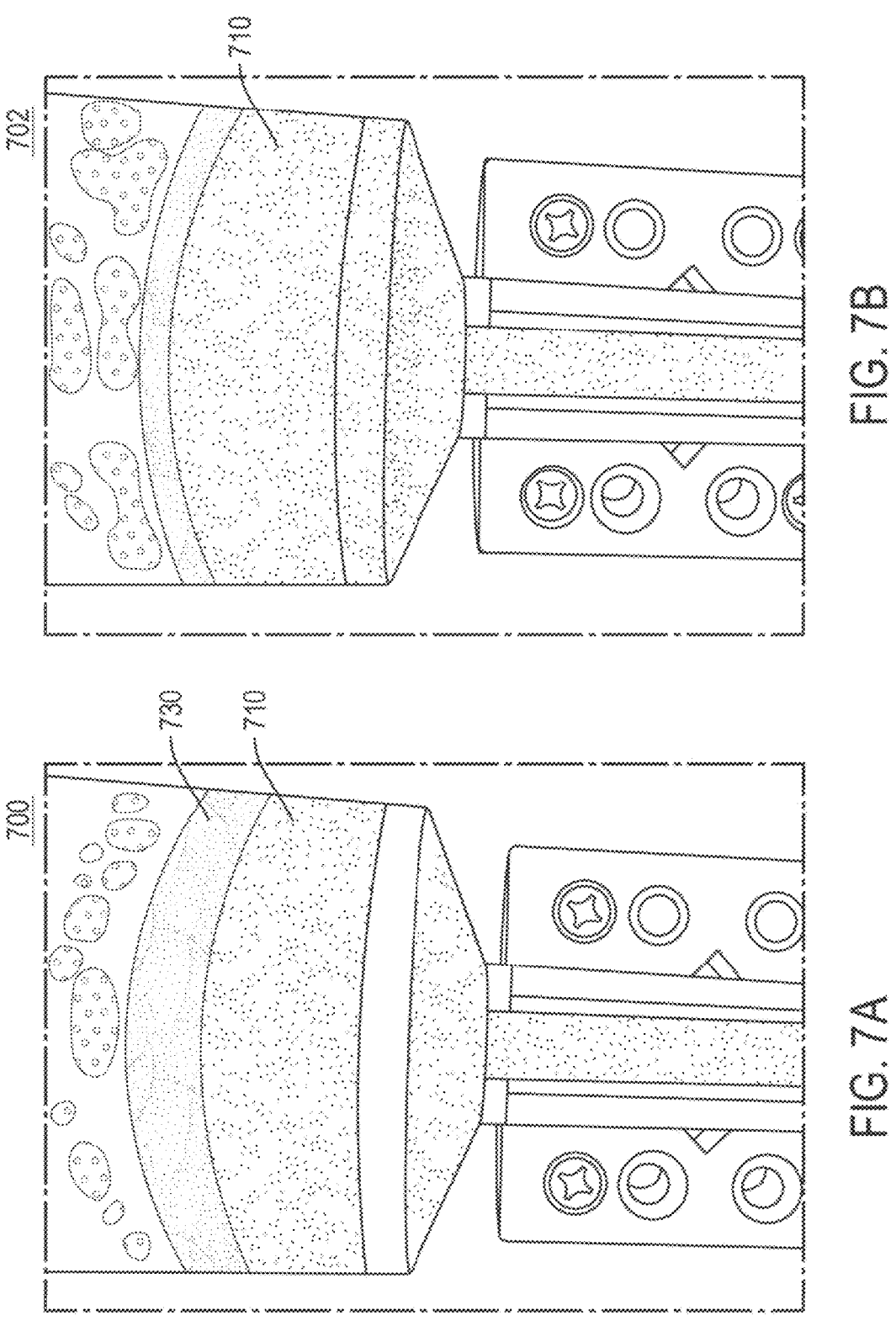
FIGS. 7A and 7B are images of blood foam in a container of a blood collection device, according to embodiments.

Moreover, conventional blood filtering systems require blood transfer between multiple syringes, which leads to the formation of substantial amounts of blood foam and blood loss. However, the blood collection devices described herein combines blood storage and filtering into a single device housing that avoids conventional blood transfer steps. Instead, blood may be output from an outlet 222, 622 of respective containers 210, 610 without generating blood foam. In some embodiments, by withdrawing blood from the container 210, 610 below a filter, any foam formed above the filter and within the container 210, 610 may remain in the container 210, 610 such that substantially all of the blood removed from the container 210, 610 is substantially free of blood foam. In some embodiments, venting to atmospheric pressure can also reduce blood foam. As shown in image 700 of FIG. 7A, blood foam 730 formed in the container 710 on a surface of the blood. The container 710 can include a vent. And as shown in image 702 of FIG. 7A, venting to atmospheric pressure via the vent can reduce blood foam in the container 710 such that the blood in the container 710 is also substantially free of blood foam.

II. Methods

Also described here are methods for processing fluid from a patient using the systems and devices described herein. In particular, the systems and devices described herein can be configured to remove a thrombus and facilitate autologous blood transfusion with minimal blood loss. Methods of using such systems and devices can include, for example, activating a vacuum source to apply negative suction through a blood collection device and catheter, filter the aspirated fluid, and bring the fluid to atmosphere pressure while minimizing hemolysis and foaming. The processed fluid may be transfused (e.g., returned) to the patient.

Figure 8:
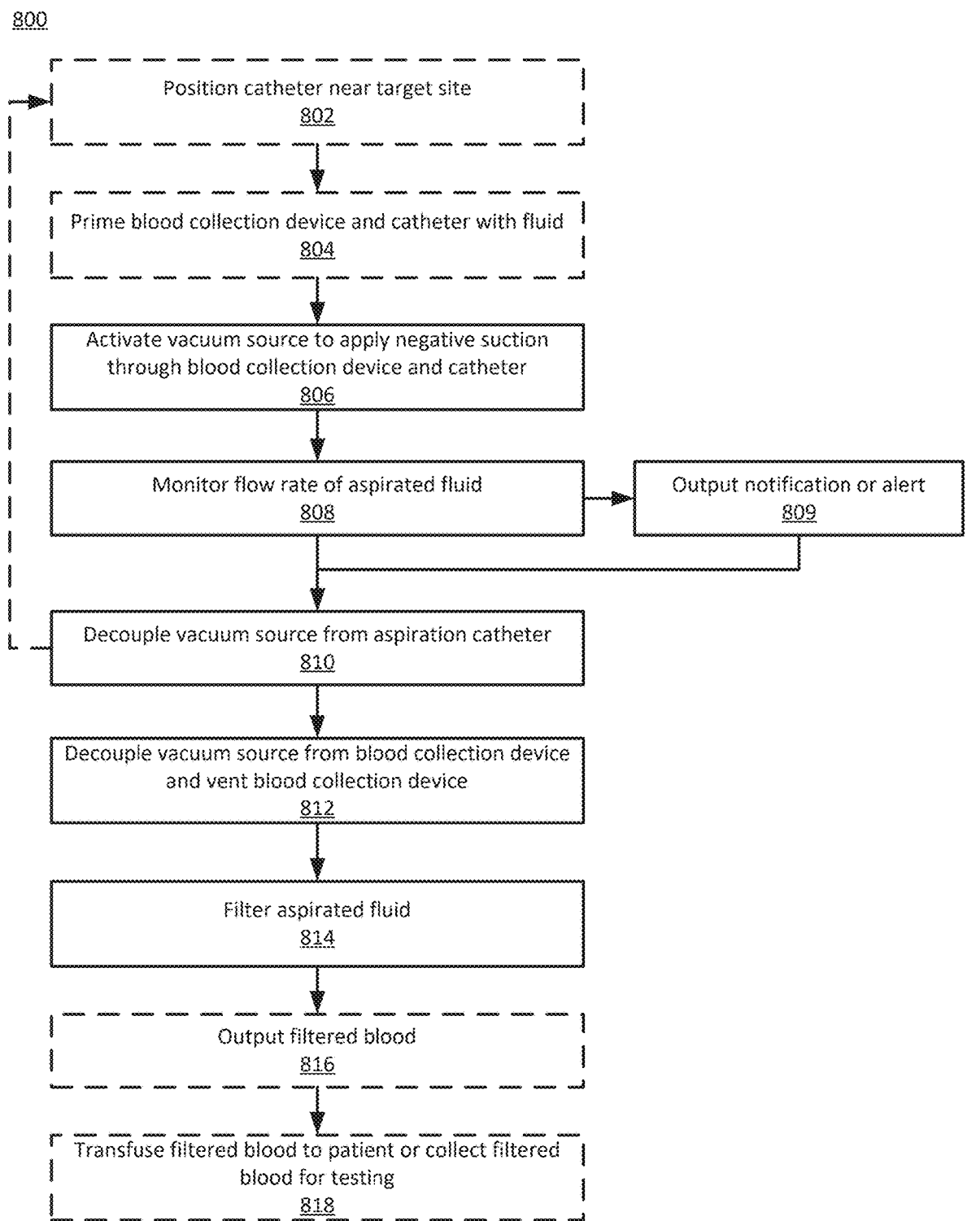
FIG. 8 is a flow chart of a method for processing blood, according to embodiments.

FIG. 8 is a flow chart of a method 800 for processing blood, e.g., using a blood collection device (e.g., blood collection device 100) coupled to an aspiration catheter (e.g., catheter assembly 10) of a thrombectomy system. At 802, a catheter (e.g., aspiration catheter, thrombectomy device, catheter assembly 10) may optionally be positioned near a target site (e.g., adjacent a thrombus). For example, an aspiration catheter may include a distal end disposed within patient vasculature near clot material. In some embodiments, the target site may be disposed within pulmonary vasculature. The catheter may be coupled to a fluid conduit and a blood collection device as described herein.

Optionally, at 804, one or more of the blood collection device, the fluid conduit, and the catheter may be primed with a fluid (e.g., saline or other priming fluid) in order to remove trapped air within a container (e.g., container 110, 210) of the blood collection device, fluid conduit (e.g., fluid conduit 152, 252), and/or catheter to prevent an air embolism and reduce blood foaming and hemolysis that otherwise contribute to blood loss. For example, a first volume of fluid may be delivered into a reservoir of the container to fill a space downstream of a filter (e.g., disposed in the reservoir with the first volume of fluid in order to submerge the filter with the fluid and prime the system.

At 806, a vacuum source may be activated (or coupled to the aspiration catheter) to apply negative suction through the blood collection device, the catheter, and conduits coupled therebetween. In some embodiments, the vacuum source can be a continuous vacuum, and the physician can actuate an actuator (e.g., button, slider, etc.) on a handpiece of the aspiration catheter to couple the lumen of the aspiration catheter to the vacuum source. The coupling of the vacuum source with the aspiration catheter can then activate vacuum suction within the catheter to draw thrombus or clot out of the patient. In some embodiments, a physician can monitor the fluid flow in the catheter and/or wait for a predefined period of time after activating suction or vacuum pressure to determine whether the thrombectomy is completed. In some embodiments, the physician can manually pause the negative pressure using the actuator disposed on the handpiece of the aspiration catheter, as described herein. For example, when the actuator is released, the actuator may be configured to close a valve that terminates aspiration of the blood or the clot material. Manual control of vacuum pressure facilitates precise control of suction and may reduce periprocedural blood loss relative to constant negative pressure applied in the lumen of the catheter.

The vacuum source, when coupled to the aspiration catheter, can aspirate a thrombus and fluid through the catheter. For example, the vacuum source can generate sufficient negative pressure to draw in the thrombus and fluid (e.g., blood including particulates) into a distal end of the catheter, and can cause the thrombus to move proximally within the lumen of the catheter, through the fluid conduit, and into the blood collection device. The thrombus and fluid can be received in the container of the blood collection device as a second volume of fluid. The amount or level of negative suction may be controlled. For example, the vacuum source can be configured to generate negative pressure within the container at a pressure level that is sufficient to cause a volume of the fluid to be drawn into the reservoir via the fluid path (e.g., catheter) while remaining greater than the vapor pressure of the fluid in the container (e.g., blood), e.g., to avoid gases dissolved within the volume of the fluid from separating from the fluid. In some embodiments, the vacuum pressure may be constant. In some embodiments, the vacuum pressure can be set to different levels.

When fluid is being aspirated and collected by the blood collection device, a flow sensor may determine a flow rate of the fluid within the system (e.g., fluid conduit coupled between the catheter and blood collection device), at 808. The flow sensor can monitor the flow rate to determine when the flow rate is greater than a predetermined threshold. A fast flow rate (e.g., a flow rate greater than the predetermined threshold) can be indicative of blood being aspirated without clot (and therefore unproductive aspiration of clot). A slow flow rate (e.g., a flow rate less than the predetermined threshold) can be indicative of clot being captured and/or ingested by the aspiration catheter.

At 809, when the flow rate is fast (e.g., above a predetermined threshold), then a notification or alert may be output to the user that the fluid flow rate has exceeded the predetermined threshold upon determination that the fluid flow rate is above the predetermined threshold. For example, the notification may include one or more of an audio and visual output (e.g., audible signal, flashing light).

At 810, the user may decouple the vacuum source from the aspiration catheter in response to the notification. In this manner, the user remains in full control of the suction and procedure. The decoupling of the vacuum source may minimize the amount of blood removed from the patient such that the amount of blood to be processed and transfused to the patient may also be minimized. As described above, the user can decouple the vacuum source from the aspiration catheter by releasing an actuator on a handle of the aspiration catheter or other catheter device. Alternatively, the vacuum source can be deactivated or decoupled from the aspiration catheter automatically in conjunction with the notification, e.g., as implemented using processor control. If further aspiration is needed (e.g., to remove additional clot material), the physician can reposition the catheter, at 802, and then reactive the vacuum, at 806.

At 812, the user can decouple the vacuum source from the blood collection device. For example, the volume of fluid received in the container of the blood collection device may fill the container to a certain level (e.g., a maximum fill line), and it may be necessary to reduce the level of fluid within the container before performing further aspiration. Alternatively, or additionally, the user may determine that the thrombus has been removed and end the procedure. In such cases, the user can decouple the vacuum source from the blood collection device, e.g., using an actuator (e.g., of a selector valve, such as, for example, selector valve 140). Further, at 812, the pressure in the blood collection device may be increased from vacuum pressure to atmospheric pressure at a predetermined rate, e.g., using one or more vents coupled to or integrated with the container of the blood collection device. As described herein, controlled venting of the vacuumed blood may reduce blood foaming and hemolysis to minimize blood loss and enable a higher percentage of blood to be reinjected into the patient. For example, after decoupling the vacuum source from the blood collection device, a vent may be coupled to the reservoir to vent air into the reservoir at an average rate that prevents turbulent movement of at least the second volume of fluid within the reservoir. For example, the average rate of pressure change during venting may be less than about 15 inHg per second.

At 814, fluid received in the blood collection device from the catheter may be filtered using one or more filters disposed in the reservoir. For example, the blood collection device may receive the fluid including a thrombus and blood into the container, which can include one or more filters. The thrombus and other particulates may be filtered out using the one or more filters, and the filtered blood may be received in a region of the container for being withdrawn. In some embodiments, a first filter having openings of a first size may filter particulates within the volume of blood having a size greater than the first size. After filtering using the first filter, a second filter having openings of a second size may filter particulates within the volume of blood having a size greater than the second size, the second size being smaller than the first size. In some embodiments, fluid including thrombus entering the container of the blood collection device can pass through the first filter (e.g., a coarse filter) and then remain above the second filter (e.g., a fine filter). When an extraction device is then coupled to the outlet (e.g., outlet 120), the extraction device can be used to generate suction or negative pressure to create a pressure differential across the second filter to drive the fluid through the second filter to further filter particulates from the fluid.

Optionally, at any of the steps of method 800, the user may switch the fluid connections of the system (e.g., using a valve) to couple or isolate the blood collection device from the catheter and vacuum source. For example, in a first configuration, a user can fluidically couple the catheter to the blood collection device and the vacuum source to the blood collection device, to cause fluid (e.g., blood with clot material) to be drawn into the blood collection device. In a second configuration, a user can decouple the catheter from the blood collection device and couple a vent to the blood collection device, to cause pressure within the container of the blood collection device to increase to atmospheric pressure. As described above, the vent can be coupled to the container via a fluid conduit that is the same as the vacuum source (e.g., vacuum conduit) or a different fluid conduit or port.

At 816, filtered blood may optionally be output from the blood collection device. For example, an extraction device can be coupled to the outlet of the blood collection device (e.g., outlet 120), and the extraction device can be used to draw the fluid within the container of the blood collection device out through the outlet. As described above, in some embodiments, the fluid within the container can be drawn through a fine filter due to suction applied by the blood collection device. The filtered blood may be output from the blood collection device into the extraction device. In some embodiments, the extraction device can be a syringe. The output blood may then be used for transfusion and/or blood sampling analysis.

At 818, filtered blood may optionally be transferred to the patient or collected for testing. In some embodiments, the extraction device may be decoupled from the outlet. A portion of the filtered blood may be reinfused back into the patient using the extraction device. For example, the syringes may be coupled to a fluid port of the catheter and transfused into the patient. In some embodiments, the steps of method 800 may each be performed within a sterile barrier.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The specific examples and descriptions herein are exemplary in nature and embodiments may be developed by those skilled in the art based on the material taught herein without departing from the scope of the present invention.

The invention claimed is:

1. An apparatus, comprising:
   a fluid conduit configured to receive a volume of fluid from a patient, the volume of fluid including a plurality of particulates having different sizes;
   a container including an inlet near a first end and an outlet near a second end opposite the first end, the inlet being fluidically coupled to the fluid conduit, the container defining a reservoir configured to receive the volume of fluid from the fluid conduit via the inlet;
   a first filter disposed within the reservoir downstream from the inlet, the first filter including openings having a first size and being configured to filter particulates from the plurality of particulates having a size greater than the first size; and
   a second filter disposed within the reservoir downstream from the first filter and upstream of the outlet, the second filter being separate from the first filter and disposed near the second end of the container, the second filter including openings having a second size and being configured to filter particulates from the plurality of particulates having a size greater than the second size, the second size being smaller than the first size,
   the outlet being couplable to a vacuum source that can generate negative pressure to draw at least a portion of the volume of fluid within the reservoir through the second filter and into the vacuum source.

2. The apparatus of claim 1, wherein the volume of fluid is a first volume of fluid, the outlet further being configured to receive, before the first volume of fluid is received in the container, a second volume of fluid into the reservoir to fill at least a section of the reservoir disposed downstream of the second filter.

3. The apparatus of claim 1, wherein the volume of fluid is a first volume of fluid, the outlet further being configured to receive, before the first volume of fluid is received in the container, a second volume of fluid into the reservoir to submerge the second filter and fill a section of the reservoir disposed downstream of the second filter.

4. The apparatus of claim 1, wherein the second filter includes a two-layer filter or a three-layer filter.

5. The apparatus of claim 1, further comprising a vacuum conduit disposed near the first end of the container at a location spaced from the inlet, the vacuum conduit configured to generate a negative pressure within the reservoir to draw the volume of fluid into the reservoir.

6. The apparatus of claim 1, further comprising a vent that is couplable to the reservoir via a line that is attached to the container at a location near the first end of the container and spaced from the inlet, the vent, when coupled to the reservoir, configured to vent air into the reservoir.

7. The apparatus of claim 6, wherein the vent has a cross-sectional area of between about 0.05 mm$^2$ and about 1.5 mm$^2$.

8. The apparatus of claim 6, wherein the container includes a marking indicating a maximum fluid fill line, and the vent is couplable to the reservoir via a port coupled to the container at a location above the marking to reduce mixing of vented air and the volume of fluid.

9. The apparatus of claim 6, wherein the vent is configured to vent the air into the reservoir at an average rate that avoids turbulent movement of the volume of fluid within the reservoir.

10. The apparatus of claim 6, wherein an average rate of pressure change during venting is less than about 15 inHg per second.

11. The apparatus of claim 6, further including a valve configured to isolate the reservoir from the vacuum source, wherein the vent is configured to vent air into the reservoir to bring pressure within the reservoir back to atmospheric pressure after the reservoir is isolated from the vacuum source via the valve.

12. The apparatus of claim 1, wherein the outlet is couplable to an extraction device and configured to deliver the fluid filtered by the second filter into the extraction device.

13. The apparatus of claim 1, further comprising a flow sensor configured to monitor a flow rate of fluid within the fluid conduit.

14. The apparatus of claim 13, further comprising a vacuum conduit disposed near the first end of the container at a location spaced from the inlet, the vacuum conduit configured to generate a negative pressure within the reservoir to draw the volume of fluid into the reservoir,
   wherein the flow sensor includes a differential pressure switch, the differential pressure switch configured to detect when a pressure difference between the vacuum conduit and the fluid conduit is greater than a predetermined threshold.

15. The apparatus of claim 14, wherein the differential pressure switch is configured to be disposed at a location that is fluidically upstream from the reservoir by between about 2 feet and about 20 feet.

16. The apparatus of claim 14, further comprising:
   an output device configured to generate a user-perceptible signal indicative of a high flow rate in the fluid conduit,
   the differential pressure switch configured to activate the output device to generate the user-perceptible signal when the pressure difference between the vacuum conduit and the fluid conduit is greater than the predetermined threshold.

17. The apparatus of claim 1, further comprising a float valve disposed in the reservoir and configured to prevent fluid within the reservoir from overflowing the reservoir.

18. The apparatus of claim 1, wherein the volume of fluid includes blood, and the apparatus further comprises:
   a vacuum regulator configured to maintain pressure within the reservoir higher than a vapor pressure of the blood.

19. The apparatus of claim 1, wherein the volume of fluid includes blood, and the fluid conduit is coupled between an aspiration catheter disposed in the patient and the container, the fluid conduit having a cross-sectional area that remains the same or increases in a direction of flow toward the container to avoid a decrease in pressure below a vapor pressure of the blood.

20. The apparatus of claim 19, wherein the fluid conduit has an inner diameter of between about 0.15 inches and about 0.3 inches.

\*  \*  \*  \*  \*